US011357526B2

(12) United States Patent
Steger

(10) Patent No.: US 11,357,526 B2
(45) Date of Patent: *Jun. 14, 2022

(54) MEDICAL INSTRUMENT WITH SNAKE WRIST STRUCTURE

(71) Applicant: Intuitive Surgical Operations, Inc., Sunnyvale, CA (US)

(72) Inventor: John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 395 days.

This patent is subject to a terminal disclaimer.

(21) Appl. No.: 16/432,547

(22) Filed: Jun. 5, 2019

(65) Prior Publication Data

US 2019/0282253 A1    Sep. 19, 2019

Related U.S. Application Data

(63) Continuation of application No. 14/854,460, filed on Sep. 15, 2015, now Pat. No. 10,335,177, which is a continuation of application No. 13/360,452, filed on Jan. 27, 2012, now Pat. No. 9,161,771.

(60) Provisional application No. 61/486,065, filed on May 13, 2011.

(51) Int. Cl.
*A61B 17/29* (2006.01)
*A61B 34/30* (2016.01)
*A61B 17/00* (2006.01)

(52) U.S. Cl.
CPC .............. *A61B 17/29* (2013.01); *A61B 34/30* (2016.02); *A61B 2017/00314* (2013.01); *A61B 2017/2908* (2013.01); *A61B 2034/306* (2016.02)

(58) Field of Classification Search
CPC combination set(s) only.
See application file for complete search history.

(56) References Cited

U.S. PATENT DOCUMENTS

| 1,820,463 A | 8/1931 | Klein |
| 3,060,972 A | 10/1962 | Sheldon |
| 3,071,161 A | 1/1963 | Ulrich |
| 3,190,286 A | 6/1965 | Stokes |
| 3,557,780 A | 1/1971 | Sato |
| 3,605,725 A | 9/1971 | Bentov |
| 4,466,649 A | 8/1984 | Ozawa |

(Continued)

FOREIGN PATENT DOCUMENTS

| CA | 2853431 A | 5/2013 |
| EP | 0165718 A2 | 12/1985 |

(Continued)

OTHER PUBLICATIONS

Matsen et al. ("Diagnosis and Management of Compartmental Syndromes," 1980) (Year: 1980).*

(Continued)

*Primary Examiner* — Scott Luan

(57) ABSTRACT

A medical instrument includes a snake wrist structure further including: a first joint disk having a first rim having a first tooth slot and a first toothed gear with the first tooth slot opposite the first toothed gear along the first rim; and a first strut having a first slot bearing and a first hole bearing connected by a first connection strut with the first slot bearing in the first tooth slot.

21 Claims, 19 Drawing Sheets

(56) References Cited

U.S. PATENT DOCUMENTS

| | | |
|---|---|---|
| 4,489,826 A | 12/1984 | Dubson |
| 4,580,551 A | 4/1986 | Siegmund et al. |
| 4,700,693 A | 10/1987 | Lia et al. |
| 4,711,248 A * | 12/1987 | Steuer ............ A61B 5/4041 |
| | | 600/561 |
| 4,763,669 A | 8/1988 | Jaeger |
| 4,790,294 A | 12/1988 | Allred, III et al. |
| 4,834,761 A | 5/1989 | Walters |
| 4,854,626 A | 8/1989 | Duke |
| 4,880,015 A | 11/1989 | Nierman |
| 4,984,951 A | 1/1991 | Jameson |
| 5,174,276 A | 12/1992 | Crockard |
| 5,257,618 A | 11/1993 | Kondo |
| 5,271,381 A | 12/1993 | Ailinger et al. |
| 5,273,026 A | 12/1993 | Wilk |
| 5,286,228 A | 2/1994 | Lee et al. |
| 5,297,443 A | 3/1994 | Wentz |
| 5,314,424 A | 5/1994 | Nicholas |
| 5,322,064 A | 6/1994 | Lundquist |
| 5,325,845 A | 7/1994 | Adair |
| 5,330,502 A | 7/1994 | Hassler et al. |
| 5,354,162 A | 10/1994 | Burdea et al. |
| 5,381,782 A | 1/1995 | Delarama et al. |
| 5,403,342 A | 4/1995 | Tovey et al. |
| 5,405,344 A | 4/1995 | Williamson et al. |
| 5,425,743 A | 6/1995 | Nicholas |
| 5,441,494 A | 8/1995 | Ortiz |
| 5,454,827 A | 10/1995 | Aust et al. |
| 5,476,479 A | 12/1995 | Green et al. |
| 5,486,154 A | 1/1996 | Kelleher |
| 5,490,819 A | 2/1996 | Nicholas et al. |
| 5,498,256 A | 3/1996 | Furnish |
| 5,513,827 A | 5/1996 | Michelson |
| 5,520,678 A | 5/1996 | Heckele et al. |
| 5,522,788 A | 6/1996 | Kuzmak |
| 5,549,636 A | 8/1996 | Li |
| 5,562,699 A | 10/1996 | Heimberger et al. |
| 5,570,919 A | 11/1996 | Eusebe |
| 5,599,151 A | 2/1997 | Daum et al. |
| 5,609,601 A | 3/1997 | Kolesa et al. |
| 5,620,415 A | 4/1997 | Lucey et al. |
| 5,624,398 A | 4/1997 | Smith et al. |
| 5,626,608 A | 5/1997 | Cuny et al. |
| 5,632,432 A | 5/1997 | Schulze et al. |
| 5,643,294 A | 7/1997 | Tovey et al. |
| 5,647,743 A | 7/1997 | Schmitt |
| 5,702,408 A | 12/1997 | Wales et al. |
| 5,704,534 A | 1/1998 | Huitema et al. |
| 5,713,505 A | 2/1998 | Huitema |
| 5,716,352 A | 2/1998 | Viola et al. |
| 5,759,151 A | 6/1998 | Sturges |
| 5,792,164 A | 8/1998 | Lakatos et al. |
| 5,807,376 A | 9/1998 | Viola et al. |
| 5,813,813 A | 9/1998 | Daum et al. |
| 5,823,066 A | 10/1998 | Huitema et al. |
| 5,827,323 A | 10/1998 | Klieman et al. |
| 5,836,960 A | 11/1998 | Kolesa et al. |
| 5,845,540 A | 12/1998 | Rosheim |
| 5,846,183 A | 12/1998 | Chilcoat |
| 5,873,817 A | 2/1999 | Kokish et al. |
| 5,899,425 A | 5/1999 | Corey, Jr. et al. |
| 5,916,146 A | 6/1999 | Allotta et al. |
| 5,916,147 A | 6/1999 | Boury |
| 5,921,956 A | 7/1999 | Grinberg et al. |
| 5,938,678 A | 8/1999 | Zirps et al. |
| 5,947,984 A | 9/1999 | Whipple |
| 5,961,532 A | 10/1999 | Finley et al. |
| 6,019,722 A | 2/2000 | Spence et al. |
| 6,050,996 A | 4/2000 | Schmaltz et al. |
| 6,161,543 A | 12/2000 | Cox et al. |
| 6,250,532 B1 | 6/2001 | Green et al. |
| 6,270,453 B1 | 8/2001 | Sakai |
| 6,464,704 B2 | 10/2002 | Schmaltz et al. |
| 6,471,641 B2 | 10/2002 | Sakamoto |
| 6,471,696 B1 | 10/2002 | Berube et al. |
| 6,482,149 B1 | 11/2002 | Torii |
| 6,491,626 B1 | 12/2002 | Stone et al. |
| 6,571,042 B1 | 5/2003 | Kordahi |
| 6,626,824 B2 | 9/2003 | Ruegg et al. |
| 6,635,071 B2 | 10/2003 | Boche et al. |
| 6,638,213 B2 | 10/2003 | Ogura et al. |
| 6,638,287 B2 | 10/2003 | Danitz et al. |
| RE38,335 E | 11/2003 | Aust et al. |
| 6,641,528 B2 | 11/2003 | Torii |
| 6,644,532 B2 | 11/2003 | Green et al. |
| 6,666,854 B1 | 12/2003 | Lange |
| 6,669,254 B2 | 12/2003 | Thom et al. |
| 6,676,676 B2 | 1/2004 | Danitz et al. |
| 6,682,541 B1 | 1/2004 | Gifford, III et al. |
| 6,743,239 B1 | 6/2004 | Kuehn et al. |
| 6,746,443 B1 | 6/2004 | Morley et al. |
| 6,749,560 B1 | 6/2004 | Konstorum et al. |
| 6,752,823 B2 | 6/2004 | Prestel |
| 6,764,445 B2 | 7/2004 | Ramans et al. |
| 6,773,327 B1 | 8/2004 | Felice et al. |
| 6,817,972 B2 | 11/2004 | Snow |
| 6,824,548 B2 | 11/2004 | Smith et al. |
| 6,843,794 B2 | 1/2005 | Sixto, Jr. et al. |
| 6,858,005 B2 | 2/2005 | Ohline et al. |
| 6,902,560 B1 | 6/2005 | Morley et al. |
| 6,942,613 B2 | 9/2005 | Ewers et al. |
| 6,945,979 B2 | 9/2005 | Kortenbach et al. |
| 6,960,162 B2 | 11/2005 | Saadat et al. |
| 6,960,163 B2 | 11/2005 | Ewers et al. |
| 6,976,969 B2 | 12/2005 | Messerly |
| 6,994,700 B2 | 2/2006 | Elkins et al. |
| 7,090,637 B2 | 8/2006 | Danitz et al. |
| 7,090,683 B2 | 8/2006 | Brock et al. |
| 7,138,976 B1 | 11/2006 | Bouzit et al. |
| 7,147,650 B2 | 12/2006 | Lee |
| 7,169,141 B2 | 1/2007 | Brock et al. |
| 7,214,230 B2 | 5/2007 | Brock et al. |
| 7,320,700 B2 | 1/2008 | Cooper et al. |
| 7,338,505 B2 | 3/2008 | Belson |
| 7,371,210 B2 | 5/2008 | Brock et al. |
| 7,410,483 B2 | 8/2008 | Danitz et al. |
| 7,480,600 B2 | 1/2009 | Massie et al. |
| 7,608,083 B2 | 10/2009 | Lee et al. |
| 7,615,066 B2 | 11/2009 | Danitz et al. |
| 7,678,117 B2 | 3/2010 | Hinman et al. |
| 7,682,307 B2 | 3/2010 | Danitz et al. |
| 7,785,252 B2 | 8/2010 | Danitz et al. |
| 8,142,421 B2 | 3/2012 | Cooper et al. |
| 8,597,280 B2 | 12/2013 | Cooper et al. |
| 9,161,771 B2 | 10/2015 | Steger |
| 9,259,275 B2 | 2/2016 | Burbank |
| 10,335,177 B2 | 7/2019 | Steger |
| 10,524,870 B2 | 1/2020 | Saraliev et al. |
| 10,550,918 B2 | 2/2020 | Cooper et al. |
| 10,682,141 B2 | 6/2020 | Moore et al. |
| 2001/0023313 A1 | 9/2001 | Ide |
| 2001/0042766 A1 | 11/2001 | Ming-Shun |
| 2002/0096177 A1 | 7/2002 | Toti et al. |
| 2002/0111604 A1 | 8/2002 | Doyle et al. |
| 2002/0156497 A1 | 10/2002 | Nagase et al. |
| 2002/0161281 A1 | 10/2002 | Jaffe et al. |
| 2002/0177750 A1 | 11/2002 | Pilvisto et al. |
| 2003/0036748 A1 | 2/2003 | Cooper et al. |
| 2003/0050649 A1 | 3/2003 | Brock et al. |
| 2003/0078644 A1 | 4/2003 | Phan |
| 2003/0109898 A1 | 6/2003 | Schwarz et al. |
| 2003/0114838 A1 | 6/2003 | ONeill et al. |
| 2003/0135204 A1 | 7/2003 | Lee et al. |
| 2003/0149338 A1 | 8/2003 | Francois et al. |
| 2003/0153902 A1 | 8/2003 | Doyle et al. |
| 2003/0229271 A1 | 12/2003 | Briscoe et al. |
| 2003/0233026 A1 | 12/2003 | Saadat et al. |
| 2004/0054322 A1 | 3/2004 | Vargas |
| 2004/0138529 A1 | 7/2004 | Wiltshire et al. |
| 2004/0138700 A1 | 7/2004 | Cooper et al. |
| 2005/0090809 A1 | 4/2005 | Cooper et al. |
| 2005/0096694 A1 | 5/2005 | Lee |
| 2005/0119527 A1 | 6/2005 | Banik et al. |
| 2005/0273084 A1 | 12/2005 | Hinman et al. |

(56) References Cited

U.S. PATENT DOCUMENTS

| | | |
|---|---|---|
| 2006/0009759 A1 | 1/2006 | Chrisitian et al. |
| 2006/0020287 A1 | 1/2006 | Lee et al. |
| 2006/0058582 A1 | 3/2006 | Maahs et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |
| 2006/0199999 A1 | 9/2006 | Ikeda et al. |
| 2006/0201130 A1 | 9/2006 | Danitz |
| 2007/0043338 A1 | 2/2007 | Moll et al. |
| 2007/0250113 A1 | 10/2007 | Hegeman et al. |
| 2007/0287993 A1 | 12/2007 | Hinman et al. |
| 2008/0064921 A1 | 3/2008 | Larkin et al. |
| 2008/0125794 A1 | 5/2008 | Brock et al. |
| 2008/0255421 A1* | 10/2008 | Hegeman ............ A61B 1/0055 600/139 |
| 2008/0255588 A1 | 10/2008 | Hinman |
| 2008/0255608 A1 | 10/2008 | Hinman et al. |
| 2008/0262538 A1 | 10/2008 | Danitz et al. |
| 2009/0198272 A1 | 8/2009 | Kerver et al. |
| 2010/0030238 A1 | 2/2010 | Viola et al. |
| 2010/0041945 A1 | 2/2010 | Isbell, Jr. |
| 2010/0234831 A1 | 9/2010 | Hinman et al. |
| 2010/0249759 A1 | 9/2010 | Hinman et al. |
| 2010/0261964 A1 | 10/2010 | Danitz et al. |
| 2010/0261971 A1 | 10/2010 | Danitz et al. |
| 2010/0262075 A1 | 10/2010 | Danitz et al. |
| 2010/0262161 A1 | 10/2010 | Danitz et al. |
| 2010/0262180 A1 | 10/2010 | Danitz et al. |
| 2011/0022078 A1 | 1/2011 | Hinman |
| 2011/0087071 A1 | 4/2011 | Danitz et al. |
| 2011/0277580 A1 | 11/2011 | Cooper et al. |
| 2012/0095451 A1 | 4/2012 | Hegeman et al. |
| 2016/0066937 A1 | 3/2016 | Steger |

FOREIGN PATENT DOCUMENTS

| | | |
|---|---|---|
| EP | 0598618 A2 | 5/1994 |
| EP | 0836833 A2 | 4/1998 |
| EP | 1132041 A2 | 9/2001 |
| EP | 1395398 B1 | 1/2006 |
| JP | H06262549 A | 9/1994 |
| JP | 2001299768 A | 10/2001 |
| WO | WO-200110292 A1 | 2/2001 |
| WO | WO-0197694 A1 | 12/2001 |
| WO | WO-200213682 A1 | 2/2002 |
| WO | WO-2004105578 A2 | 12/2004 |
| WO | WO-2005067785 A1 | 7/2005 |
| WO | WO-2005120326 A2 | 12/2005 |
| WO | WO-2005120327 A2 | 12/2005 |

OTHER PUBLICATIONS

Matsen et. al. ("Diagnosis and Management of Compartmental Syndromes," 1980) (Year: 1980) (Year: 1980).*

Cox J.L., "The Minimally Invasive Maze-III Procedure," Operative Techniques in Thoracic and Cardiovascular Surgery, W.B. Saunders Company, 2000, vol. 5 (1), pp. 79-92.

Prasad S.M., et al., "Epicardial Ablation on the Beating Heart: Progress Towards an Off-Pump Maze Procedure." The Heart Surgery Forum, Forum Multimedia Publishing, LLC, 2002, vol. 5 (2), pp. 100-104.

Simha P.M., et al., "The Elctrocautery Maze—How I Do It," The Heart Surgery Forum, Forum Multimedia Publishing, LLC, 2001, vol. 4 (4), pp. 340-345.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

MEDICAL INSTRUMENT WITH SNAKE WRIST STRUCTURE

CROSS-REFERENCE TO RELATED APPLICATIONS

This application is a continuation of U.S. patent application Ser. No. 14/854,460 (filed Sep. 15, 2015)(entitled "MEDICAL INSTRUMENT WITH SNAKE WRIST STRUCTURE"), which is a continuation of U.S. patent application Ser. No. 13/360,452 (filed Jan. 27, 2012)(entitled "MEDICAL INSTRUMENT WITH SNAKE WRIST STRUCTURE"), which claims priority to and the benefit of U.S. Patent Application No. 61/486,065 (filed May 13, 2011) (entitled "MEDICAL INSTRUMENT WITH SNAKE WRIST STRUCTURE"), each of which is incorporated herein by reference in its entirety.

TECHNICAL FIELD

The present invention relates generally to a medical instrument, and more particularly to a medical instrument for holding a mechanism attached therein in different positions.

BACKGROUND ART

Modern tools and manipulating instruments, including instruments with jaws for performing surgical operations, such as cutting, grasping and holding, are providing increasing levels of functionality and strength to support modern needs including applications in minimally invasive and micro-surgery. However, the tools available for positioning the manipulating instruments are not efficient and often lack precision.

As instruments become smaller and stronger with the growth of material science and manufacturing, new and old paradigms begin to take advantage of the improvements. There are many technological solutions to take advantage of smaller and stronger tools. One existing approach is to use smaller tools to perform micro-surgery or minimally invasive surgery.

Often, the methods of operating the tools for performing micro-surgery are not intuitive and require special training and attention of the user. Furthermore, the tools are often not efficient in applying the correct amount of force and lack the required degree of maneuverability needed to controllably navigate complex anatomy during surgical procedures.

The need to reduce costs, improve efficiencies and performance, and meet competitive pressures adds an even greater urgency to the critical necessity for finding answers to these problems. However, solutions to these problems have been long sought but prior developments have not taught or suggested any solutions and, thus, solutions to these problems have long eluded those skilled in the art. Thus, a need still remains for manipulating device with a flexible jaw and wrist mechanism.

DISCLOSURE OF THE INVENTION

The present invention provides a medical instrument including a snake wrist structure further including a first joint disk having a first rim having a first tooth slot and a first toothed gear with the first tooth slot opposite the first toothed gear along the first rim; and a first strut having a first slot bearing and a first hole bearing connected by a first connection link with the first slot bearing in the first tooth slot.

Certain embodiments of the invention have other steps or elements in addition to or in place of those mentioned above. The steps or elements will become apparent to those skilled in the art from a reading of the following detailed description when taken with reference to the accompanying drawings.

BEST MODE FOR CARRYING OUT THE INVENTION

Figure 1:
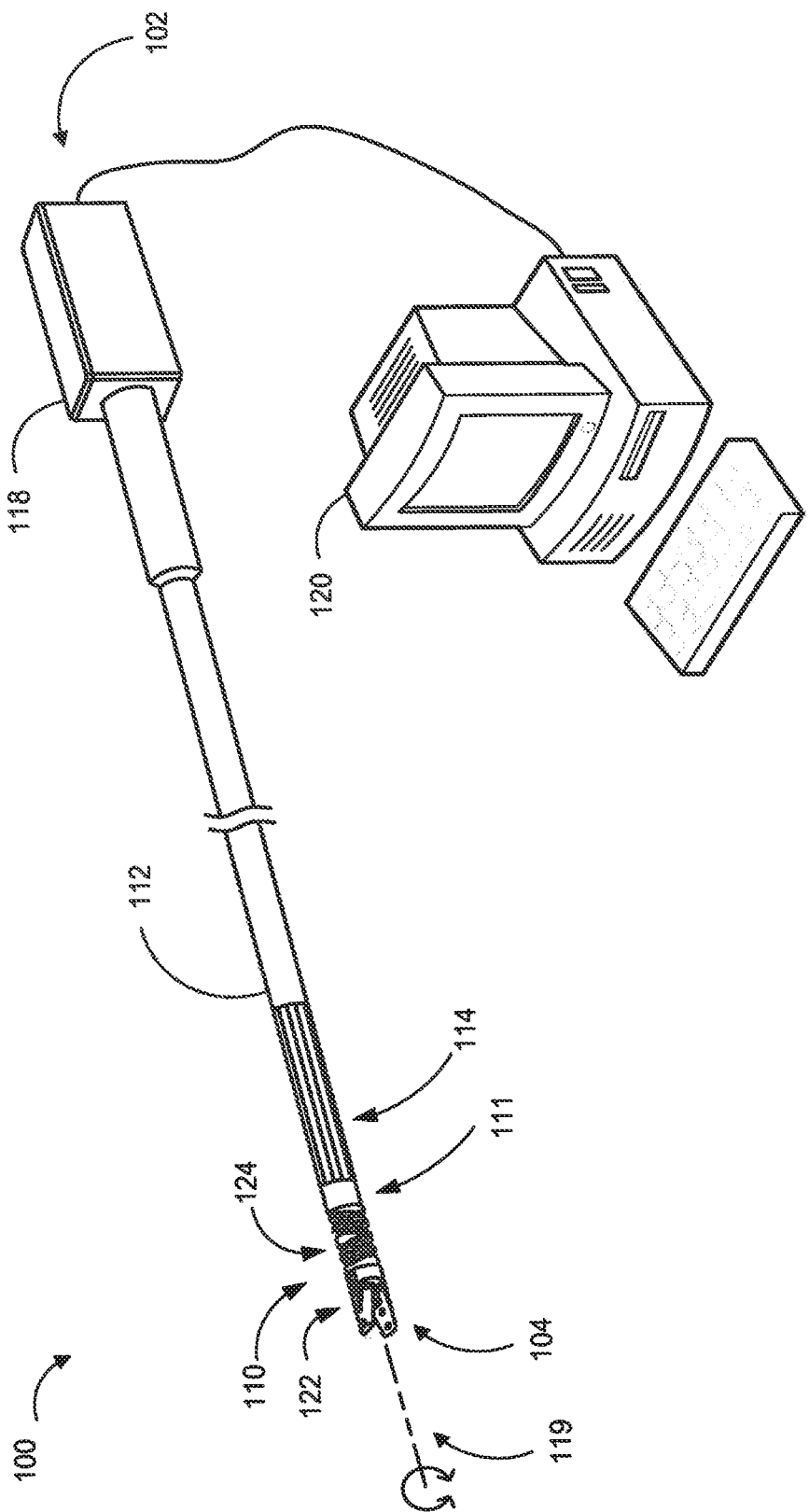
FIG. 1 is a medical instrument with a snake wrist structure in a first embodiment of the present invention.

The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known devices, instrument configurations, and process steps are not disclosed in detail.

For expository purposes, the term "horizontal" as used herein can be the horizontal direction seen when viewing the drawing as indicated by the figure designation of "FIG.". The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal, as shown in the figures. The term "directly on" means there is direct contact with no intervening element between the elements described.

Also, in the following description, connected and coupled are used to describe a relationship between two members. The term "connected" means that the two members are physically and directly joined to each other.

Different members can be connected in variety of ways. For example, different members can be connected by being formed adjacent to each other, such as through molding or carving. Also, for example, different members can be connected by being attached together, such as through adhesives, fasteners, welds, or brazing.

The term "coupled" means that the two members are physically linked through one or more other members. The phrases "reciprocating motion" and "reciprocating movement" are defined to describe a repetitive up-and-down or back-and-forth motion. The phrases "distal" and "proximal" are defined to respectively indicate the directions designated by the related arrows in FIG. 1 or along the path of connectivity between the point where the instrument couples to the robot arm (proximal) and the instrument tip that contacts surgical patient tissue (distal).

The drawings showing embodiments of the system are semi-diagrammatic and not to scale and, particularly, some of the dimensions are for the clarity of presentation and are shown exaggerated in the drawing FIGS. Similarly, although the views in the drawings for ease of description generally show similar orientations, this depiction in the FIGS. is arbitrary for the most part. Generally, the invention can be operated in any orientation.

Referring now to FIG. 1, therein is shown a medical instrument 100 with a snake wrist structure 110 in a first embodiment of the present invention. The snake wrist structure 110 is a segmented member that bends or provides multi-axis movement to change the relative position and orientation of a member attached thereon. The term "segmented" is defined as a structure including one or more individual segments or links. The snake wrist structure 110 is also supported by another connection member 111 attached thereon.

The connection member 111 is defined as a structural element that can be physically and directly joined to the snake wrist structure 110. The connection member 111 can include a variety of elements including a stationary member, a moveable member, a rotating member, an articulating member, a fixed member, or a combination thereof. The connection member 111 can be connected on either side of the snake wrist structure 110.

For example, the snake wrist structure 110 can be connected to the stationary member on one side and the moveable member on the opposite side. The stationary member can hold the snake wrist structure 110 in position and the snake wrist structure 110 can be manipulated to move and position the moveable member.

For a more specific example, the snake wrist structure 110 can have a mechanical awl attached to one side and a camera on the other side. The mechanical arm can position the snake wrist structure 110 and the camera in place. The snake wrist structure 110 can be manipulated to present different angles, orientations, and views for the camera from the given location.

The medical instrument 100 can include a proximal end 102 and a distal end 104. For example, the medical instrument 100 can include the snake wrist structure 110 near the distal end 104, a tube 112 with actuating members 114 (shown in a cutaway view of tube 112 in FIG. 1), and an actuator system 118 at the proximal end 102. The medical instrument 100 can include a tool or sensory mechanism at the distal end, such as a jaw mechanism 122, camera, probe, light, tube, cutter, or a combination thereof.

In a further example, the jaw mechanism 122 can be at the distal end 104 of the medical instrument 100. The snake wrist structure 110 can be connected to the jaw mechanism 122. The snake wrist structure 110 can have the tube 112 attached on the other side. The snake wrist structure 110 can also be coupled to the actuator system 118 through the actuating members 114. The jaw mechanism 122 can be analogous to a human hand, and the snake wrist structure 110 can be analogous to a human wrist. The jaw mechanism 122 can be a mechanical assembly, such as a gripper or a cutter.

The snake wrist structure 110 is shown having a cylindrical configuration having a central axis 119 that extends through the center of the snake wrist structure 110. The cylindrical configuration eliminates sharp edges and allows the snake wrist structure 110 and the jaw mechanism 122 to project into tight spaces and navigate complex anatomy.

The tube 112 holds the snake wrist structure 110 at a location in space. For example, the tube 112 can be straight tube of a medical instrument. For illustrative purposes, the tube 112 is shown as a hollow cylindrical member encasing the actuating members 114 within the tube 112. However, it is understood that the tube 112 can be different and have various cross-sectional shapes, or be solid and have externally the actuating members 114.

The snake wrist structure 110 can be attached at the distal end 104 of the tube 112 and the actuator system 118 at the proximal end 102. Generally, the jaw mechanism 122 is attached at the distal end 104.

The actuator system 118 exerts forces coupled by the actuating members 114 to bend the snake wrist structure 110 and to actuate the jaw mechanism 122. The actuating members 114, for example, can be a rod or cable or cable and pulley system that is pushed or pulled to bend the snake wrist structure 110 along the direction of applied force. The actuator system 118 can also be coupled through the actuating members 114 to convey the forces to cause rotating reciprocation motion of the jaw mechanism 122.

The actuator system 118 may include or may be coupled to electrical, hydraulic, or pneumatic power systems to generate the applied forces. A control system 120 can be coupled to the actuator system 118 for controlling the amount of applied forces and motion for the jaw mechanism 122 and a wrist mechanism 124. The control system 120 is a mechanism that can control the operation of the jaw mechanism 122. For example, the control system 120 can be a computer and motor assembly or an assembly of handles, gears, and levers.

Figure 2:
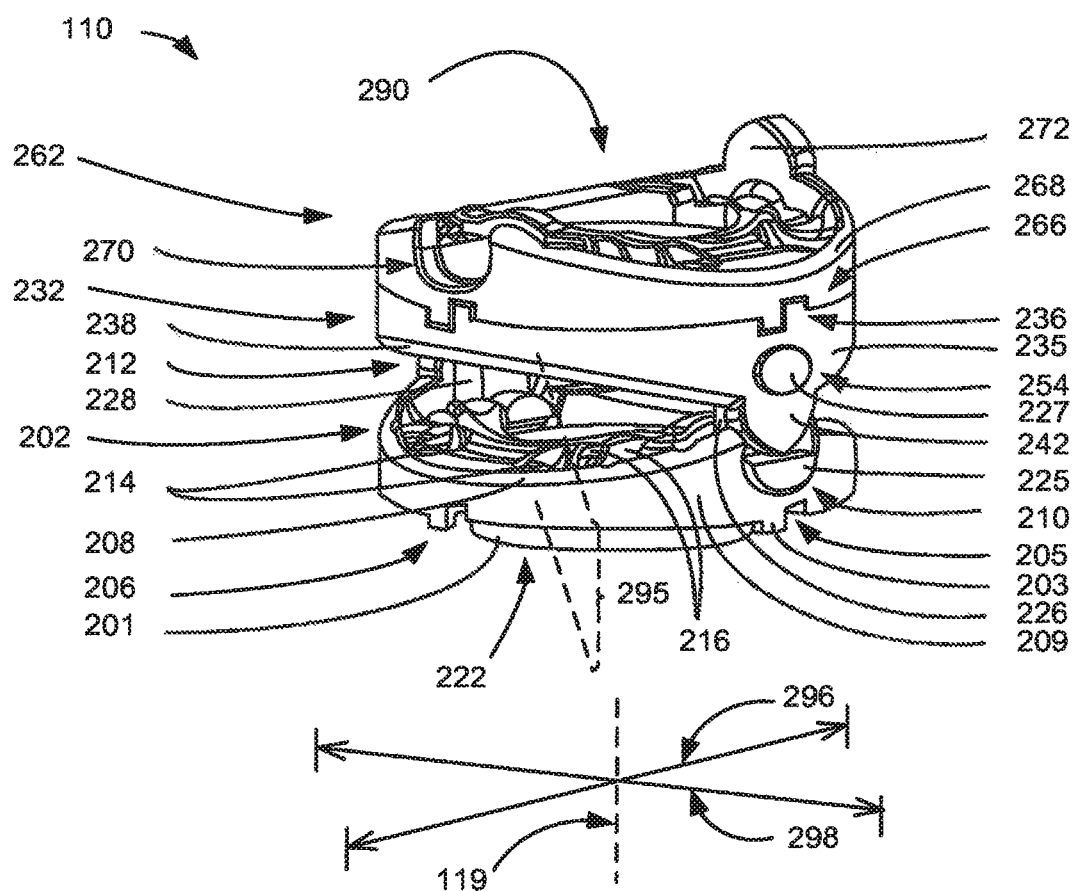
FIG. 2 is an isometric view of the snake wrist structure in a second embodiment.

Referring now to FIG. 2, therein is shown an isometric view of the snake wrist structure 110 in a second embodiment. The snake wrist structure 110 is in an unflexed configuration.

The snake wrist structure 110 can include a first locking member 201 connected to a first joint disk 202. The first locking member 201 is defined as a structural element used to connect the first joint disk 202 to another member. The first locking member 201 can be a cylindrical tube with an outer diameter approximately equal to a diameter of a first inner opening 222 of the first joint disk 202. The first locking member 201 forms a tight fit with the first inner opening 222 when connected to the first joint disk 202.

The first joint disk 202 is defined as a structural element that can be coupled to other similar joint disk elements to form the snake wrist structure 110. The first joint disk 202 can be a circular structure with a single toothed gear and a single tooth slot along the outside diameter of the first joint disk 202 for forming an articulating joint.

The snake wrist structure 110 can include the first joint disk 202. The first joint disk 202 can include a set of the first alignment keys 206, a first angled surface 208, a first rim 209, a first tooth slot 210, and a first toothed gear 212. The first joint disk 202 can include the first inner opening 222 in the center of the first joint disk 202. The first inner opening 222 is defined as the central unobstructed through lumen of the joint disk. A lumen is defined as an internal cavity or opening in a cylindrical structure. The inner openings of the coupled disks of the snake wrist structure 110 can form a snake wrist lumen 290 in the snake wrist structure 110.

The snake wrist lumen 290 is defined as a channel in the snake wrist structure 110 that can be used to pass mechanical, electrical, or optical cables or other control tubes. The snake wrist lumen 290 can also be a through lumen for providing fluid or gas delivery or extraction, or for use as a through lumen in the instrument to allow for the passage of secondary smaller diameter surgical tools through the snake joint assembly such as a biopsy needle, grasper, or laser fiber.

The first joint disk 202 can include the first alignment keys 206 around the bottom of the first joint disk 202. The first alignment keys 206 are defined as structures for connecting the first joint disk 202 with the connection member 111 of FIG. 1 in a fixed orientation and to prevent rotation of the first joint disk 202 relative to the connection member 111. The first alignment keys 206 are positioned around the bottom circumference of the first joint disk 202 distributed 90 degrees apart from one another.

The first alignment keys 206 can have a first alignment key tab 203 and a first alignment key hole 205. The first alignment key tab 203 can be an extended structure used to interlock with the first alignment key hole 205 of another element. The first alignment key hole 205 can be a hole in the first joint disk 202 where the first alignment key tab 203 of another element can fit into to lock the first joint disk 202 in place. The first alignment keys 206 can be connected to the alignment keys of another disk whereby the first alignment key tab 203 are inserted in the first alignment key hole 205 of another disk.

The first joint disk 202 can include the first tooth slot 210 in the first rim 209 of the first joint disk 202. The first tooth slot 210 is defined as an opening acting as a receiver for a toothed gear to form a pivoting joint or hinge structure. The first tooth slot 210 can be as a concave opening in the first rim 209 of the first joint disk 202. The first tooth slot 210 can receive a second toothed gear 242 to form a pivoting joint or hinge. A pivoting joint is a connection between two rigid elements where one element can pivot or rotate relative to the other element.

The first rim 209 is defined as a structural element extending around the circumference of the top of the first joint disk 202. The first rim 209 can include the first tooth slot 210, the first toothed gear 212, and the first angled surface 208.

The first joint disk 202 can include the first toothed gear 212 on the opposite side of the first rim 209 across from the first tooth slot 210. The first toothed gear 212 can be a structure that extends from the first rim 209 of the first joint disk 202 to form a pivoting joint or hinge when inserted into a matching slot. The first toothed gear 212 can be a convex shape for guiding the motion of the first joint disk 202.

As an example, the first joint disk 202 can include the first angled surface 208 around both sides the first rim 209 of the first joint disk 202 between the first toothed gear 212 to the first tooth slot 210. The first angled surface 208 can be a structural element of the first joint disk 202 used as a mechanical stop to limit the range of motion of the first joint disk 202 or other elements. The first angled surface 208 can extend in a semi-circular arc in a downward direction from the base of the first toothed gear 212 and top of the first tooth slot 210 reaching a maximum depth midway between the first toothed gear 212 and the first tooth slot 210.

In another example, the first angled surface 208 can form an angle approximately of 22.5 degrees below a plane orthogonal to the central axis 119 of FIG. 1 whereby the first joint can be articulated to a maximum angle 45 degrees from the central axis 119.

It has been discovered that the present invention provides a 50% reduction in the moment arm for the cable force component. At 45 degrees, the moment arm for the cable force component contributing to joint torque is cut in half. Further range of motion is technically possible but comes at the cost of rapidly diminishing joint torque and increased risk of cable damage due to the amount of required flex.

The first joint disk 202 can include a set of first cable holes 214. The first cable holes 214 are defined as opening for passing joint control cables through joint disks. The first cable holes 214 can be openings extending through the first joint disk 202 to provide access for the joint control cables (not shown). The joint control cables are defined as cables that are used to control the flexing of joints in the snake wrist structure 110.

The first joint disk 202 can include a set of first cable cutouts 216 around the first cable holes 214 on the same side of the first joint disk 202 as the first angled surface 208. The first cable cutouts 216 are defined as beveled areas around the first cable holes 214 to accommodate motion of the joint control cables when the snake wrist structure 110 is flexed. The snake wrist structure 110 can include a second joint disk 232. The second joint disk 232 is defined as a structural element that can be coupled to other joint disk elements to form the snake wrist structure 110. The second joint disk 232 can be a duplicate of the first joint disk 202 in an inverted and rotated position. The second joint disk 232 is mounted over the first joint disk 202 in an inverted position and rotated 180 degrees. The first joint disk 202 can be connected to the second joint disk 232 to form an articulating joint.

The second joint disk 232 can have the same configuration as the first joint disk 202. The second joint disk 232 can include the second toothed gear 242, a second angled surface 238, a second rim 235, a set of second alignment keys 236, and a second bearing hole 254.

The second joint disk 232 can include the second toothed gear 242. The second toothed gear 242 can be a structure that extends from the second rim 235 of the second joint disk 232 to form a pivoting joint or hinge when inserted into a matching slot. The second joint disk 232 can be mounted over the first joint disk 202 whereby the second toothed gear 242 is over the first tooth slot 210 of the first joint disk 202. The second toothed gear 242 can be inserted into the first tooth slot 210 of the first joint disk 202. The second toothed gear 242 can be a single toothed gear extending from the second rim 235 of the second joint disk 232. The second toothed gear 242 can have a convex shape for guiding the motion of the second joint disk 232.

The second joint disk 232 can include the second alignment keys 236. The second alignment keys 236 are on the side of the second joint disk 232 opposite from the second toothed gear 242. The second alignment keys 236 are defined as structures for connecting the second joint disk 232 with another element in a fixed orientation and to prevent rotation of the second joint disk 232 relative to the other element. For example, the other element can be another joint disk, a mounting surface, an extension element, or a combination thereof.

The second joint disk 232 can include the second angled surface 238 around both sides of the second rim 235 of the second joint disk 232. The second angled surface 238 extends in a semi-circular arc in a downward direction from the base of the second toothed gear 242 and the point opposite the second toothed gear 242 reaching a maximum depth midway between the second toothed gear 242 and point opposite the second toothed gear 242. For example, the second angled surface 238 can be formed at an angle of 22.5 degrees below a plane orthogonal to the central axis 119.

The second joint disk 232 can be coupled to the first joint disk 202 by a first strut 226 and a second strut 228. The first strut 226 can include a first hole bearing 227 and a first slot bearing 225.

The first hole bearing 227 can be a structural element forming an axis of rotation for the second joint disk 232. The first hole bearing 227 can be a cylindrical element that can bear loads.

The first slot bearing 225 can be a structural element forming an axis of rotation for the first joint disk 202. The first slot bearing 225 can be a cylindrical element that can bear loads.

The first strut 226 can attach to the second joint disk 232 with the first hole bearing 227 inserted into the second bearing hole 254. The first strut 226 can attach to the first joint disk 202 with the first slot bearing 225 inserted into the first tooth slot 210.

The snake wrist structure 110 can include a third joint disk 262. The third joint disk 262 can have the same configuration as the first joint disk 202 and the second joint disk 232. The third joint disk 262 is mounted over and directly in contact with the second joint disk 232.

The third joint disk 262 can include a set of third alignment keys 266 spaced evenly around the circumference of the bottom of the third joint disk 262. The third alignment keys 266 are defined as structures for connecting the third joint disk 262 with another element in a fixed orientation and to prevent rotation of the third joint disk 262 relative to the other element.

The third joint disk 262 can include a third tooth slot 270 and a third toothed gear 272. The third joint disk 262 is mounted over the second joint disk 232. The third joint disk 262 can be in a variety of orientations in relation to the second joint disk 232.

The third joint disk 262 can include a third angled surface 268. The third angled surface 268 extends in a semi-circular arc in an downward direction from the base of the third toothed gear 272 and the third tooth slot 270 reaching a maximum depth midway between the third toothed gear 272 and the third tooth slot 270. For example, the third angled surface 268 can be formed at an angle of 22.5 degrees below a plane orthogonal to the central axis 119.

The third joint disk 262 is connected to the second joint disk 232 whereby the second alignment keys 236 are interlocked with the third alignment keys 266. Interlocking can be connecting two elements to prevent rotation. Interlocking can occur when the first alignment key tab 203 of the second joint disk 232 are in the first alignment key hole 205 of the third joint disk 262.

The third joint disk 262 can be connected to the second joint disk 232 with an interlocking structure. The interlocking structure can include the third alignment keys 266 interlocked with the second alignment keys 236. The interlocking structure can hold the third joint disk 262 and the second joint disk 232 in a fixed orientation to one another.

For example, the third disk joint can be rotated whereby the third tooth slot 270 and the third toothed gear 272 are at right angles to the second joint disk 232. The third tooth slot 270 and the third toothed gear 272 are on the opposite side of the third joint disk 262 from the second joint disk 232.

In another example, the third joint disk 262 can be rotated 180 degrees around the central axis 119 and mounted on the second joint disk 232. By mounting the third joint disk 262 at a 180 degree angle to the second joint disk 232, the snake wrist structure 110 can flex further around the bending axis of the first joint disk 202 and the second joint disk 232.

The snake wrist structure 110 can include a joint knuckle 295. The joint knuckle 295 can be formed by connecting the first joint disk 202 to the second joint disk 232 with the first strut 226 and the second strut 228. The joint knuckle 295 can have an interconnect structure on the proximal and distal ends to facilitate connecting to a further connection member 111 of FIG. 1.

The snake wrist structure 110 has a first transverse dimension 296 and a second transverse dimension 298 along a plane orthogonal to the central axis 119. The central axis 119 is defined as an axis that extends along the center of the snake wrist structure 110 in an unflexed configuration. The first transverse dimension 296 and the second transverse dimension 298 are shown to be the same but do not need to be and may be adjusted based on the geometry of the snake wrist structure 110. In the case in which they are equal, the snake wrist structure 110 may be circular in cross section as illustrated in FIG. 2. As an example, the first transverse dimension 296 and the second transverse dimension 298 are shown to be along directions perpendicular to each other but does not necessarily required to be perpendicular.

The snake wrist structure 110 can include a variety of configuration examples. For example, the joint knuckle 295 can be a single degree of freedom joint subassembly that consists of two identical struts and two identical joint disks that combine to provide .+−0.45 degrees of motion about the joint axis.

In another example, a "single degree of freedom joint" can be constructed by joining two identical pairs of disk-and-strut where each disk has a strut attached to the disk by mating the strut's tooth-side bearing to the tooth-side bearing on the disk. Once these two pairs are built, they are joined together aligned axially but rotated 180 degrees about the central axis of the disk whereby they mesh in a complimentary fashion. This can allow each strut's slot-side bearing surface to be mated with a slot bearing-surface on each disk.

In yet another example, the "single degree of freedom joint" can be used as a repeating unit where identical copies are stacked axially along the central axis of the instrument shaft with each subsequent joint oriented whereby its pivot axis is parallel to the previous joint in the chain or rotated 90 degrees to the previous joint axis. This can allow for a snake wrist structure with multiple degrees of freedom and a range of motion in each degree of freedom in increments of 45 degrees based on how many joints are stacked with the same orientation.

In still another example, when the single degree of freedom subassemblies are stacked together, interlocking features in adjacent identical subassemblies lock the struts and disks together whereby the struts cannot be removed from the disk, even in the event of a cable failure.

Figure 3:
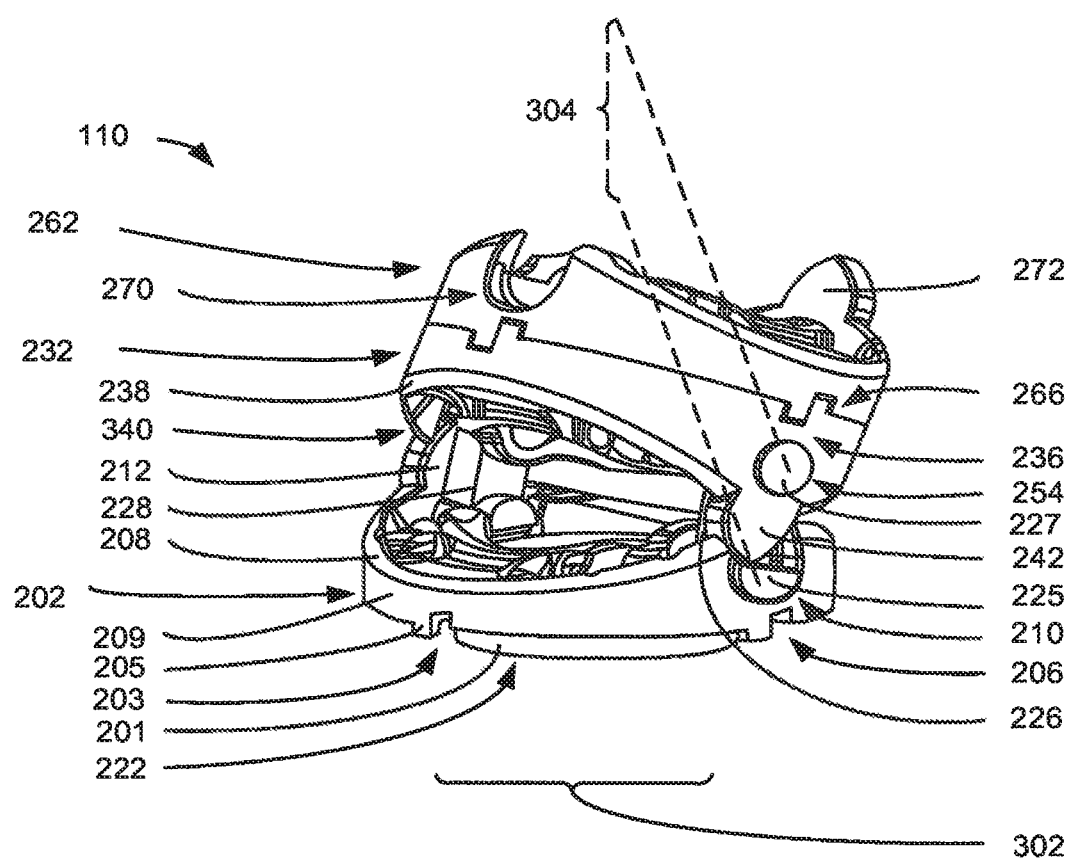
FIG. 3 is an isometric of the snake wrist structure in a flexed position in a second embodiment.

Referring now to FIG. 3 therein is shown an isometric of the snake wrist structure 110 in a flexed position in a second embodiment. The snake wrist structure 110 can include the first locking member 201 and the first joint disk 202.

The snake wrist structure 110 includes the first locking member 201 connected to the first joint disk 202. The first locking member 201 forms a tight fit with the first inner opening 222 when connected to the first joint disk 202.

The first joint disk 202 can include the first inner opening 222. The first inner opening 222 can be an opening in a central portion 302 of the first joint disk 202. The central portion 302 is defined as the interior part of the first joint disk 202 surrounding the central axis 119 of FIG. 1.

The first joint disk 202 can include first alignment keys 206 around the bottom of the circumference of the first joint disk 202. The first alignment keys 206 are distributed 90 degrees apart from one another around the bottom circumference of the first joint disk 202. The first alignment keys 206 have the first alignment key tab 203 and the first alignment key hole 205. The first alignment keys 206 can be connected to the alignment keys of another disk whereby the first alignment key tab 203 are inserted in the first alignment key hole 205 of another disk.

The first joint disk 202 can include the first tooth slot 210 on the first rim 209 of the first joint disk 202. The first joint disk 202 can include the first toothed gear 212 on the opposite side of the first rim 209 across from the first tooth slot 210.

The first joint disk 202 can include the first angled surface 208 around both sides the first rim 209 of the first joint disk 202 between the first toothed gear 212 to the first tooth slot 210. The first angled surface 208 extends in downward directions from the base of the first toothed gear 212 and top of the first tooth slot 210 reaching a maximum depth midway between the first toothed gear 212 and the first tooth slot 210. The first angled surface 208 is formed an angle of 22.5 degrees below a plane orthogonal to the central axis 119.

The snake wrist structure 110 can include the second joint disk 232. The second joint disk 232 can have the same configuration as the first joint disk 202. The second joint disk 232 is mounted over the first joint disk 202 in an inverted position and rotated 180 degrees.

The second joint disk 232 can include a second tooth slot 340 and the second toothed gear 242. The second joint disk 232 is mounted over the first joint disk 202 whereby the second tooth slot 340 is over the first toothed gear 212 and the second toothed gear 242 is over the first tooth slot 210 of the first joint disk 202. The second toothed gear 242 can be inserted into the first tooth slot 210 of the first joint disk 202. The first toothed gear 212 of the first joint disk 202 can be inserted into the second tooth slot 340.

The second joint disk 232 can include the second alignment keys 236. The second alignment keys 236 are on the side of the second joint disk 232 opposite from the second tooth slot 340 and the second toothed gear 242.

The second joint disk 232 can include the second angled surface 238 around both sides of the second rim 235 of FIG. 2 of the second joint disk 232 between the second toothed gear 242 to the second tooth slot 340. The second angled surface 238 extends in downward directions from the base of the second toothed gear 242 and top of the second tooth slot 340 reaching a maximum depth midway between the second toothed gear 242 and the second tooth slot 340. The second angled surface 238 is formed an angle of 22.5 degrees below a plane orthogonal to the central axis 119.

The second joint disk 232 can be coupled to the first joint disk 202 by a first strut 226 and the second strut 228. The first strut 226 can include a first hole bearing 227 and a first slot bearing 225.

The first strut 226 can attach to the second joint disk 232 with the first hole bearing 227 inserted into the second bearing hole 254. The first strut 226 can attach to the first joint disk 202 with the first slot bearing 225 inserted into the first tooth slot 210.

The second joint disk 232 can be in a flexed position where the second joint disk 232 is flexed around the bending axis between the first joint disk 202 and the second joint disk 232 and the second angled surface 238 is closer to the first angled surface 208 on one side of the snake wrist structure 110 and further apart on the opposite side of the snake wrist structure 110.

The snake wrist structure 110 can include the third joint disk 262. The third joint disk 262 can have the same configuration as the first joint disk 202 and the second joint disk 232. The third joint disk 262 is mounted over and directly in contact with the second joint disk 232.

The third joint disk 262 can include the third alignment keys 266 spaced evenly around the circumference of the bottom of the third joint disk 262. The third joint disk 262 is connected to the second joint disk 232 whereby the second alignment keys 236 are interlocked with the third alignment keys 266. Interlocking can be connecting two elements together to prevent rotation.

The third joint disk 262 can include the third tooth slot 270 and the third toothed gear 272. The third joint disk 262 is mounted over the second joint disk 232 whereby the third tooth slot 270 and the third toothed gear 272 are rotated 90 degrees away from the second tooth slot 340 and the second toothed gear 242. The third tooth slot 270 and the third toothed gear 272 are on the opposite side of the third joint disk 262 from the second joint disk 232.

The snake wrist structure 110 can flex in a variety of ways with different degrees of freedom. For example, when the second joint disk 232 is flexed toward one side of the snake wrist structure 110, the angular degree of flex is limited by the geometry of the first angled surface 208 and the second angled surface 238. The range of motion of the second joint disk 232 is limited by when the first angled surface 208 and the second angled surface 238 meet and prevent further motion. For example, the second joint disk 232 can only flex a maximum of 45 degrees if when the first angled surface 208 and the second angled surface 238 each form a 22.5 degree angle from the horizontal plane.

The first joint disk 202, the second joint disk 232, and the third joint disk 262 can all have the same configuration. For example, the second joint disk 232 and the third joint disk 262 can be identical versions of the first joint disk 202.

It has been discovered that the present invention provides the medical instrument 100 with simplified manufacturing. Having the first joint disk 202 and the second joint disk 232 with the same configuration can simplify the manufacture of the snake wrist structure 110 by reducing the number of unique parts required for assembly. Reducing the number of parts can simplify manufacturing complexity and reduce manufacturing cost.

The first toothed gear 212 and the second tooth slot 340 form a rolling joint 304 between the first joint disk 202 and the second joint disk 232. The rolling joint 304 is defined as a structure that forms a multi-axis joint between two elements having multiple degrees of freedom. The rolling joint 304 can be the structure where the first joint disk 202 and the second joint disk 232 join to creates a rolling motion where the path of the second joint disk 232 with respect to first joint disk 202 is defined as the same path as that of the centroid of one circle rolling on the circumference of an identical circle where each circle has a diameter equal to the distance between first slot bearing 225 and first hole bearing 227.

As the snake wrist structure 110 is flexed, the second joint disk 232 pivots around the first toothed gear 212 in the second tooth slot 340. The first toothed gear 212 coupled with the second tooth slot 340 provide a constraint with an involute profile on the shape of the first toothed gear 212 enforcing the rolling motion of the joint. The involute profile of the tooth is defined by the path traced by a point on the circumference of a circle rolling on an identical circle where each circle has a diameter equal to the distance first slot bearing 225 and first hole bearing 227.

Figure 4:
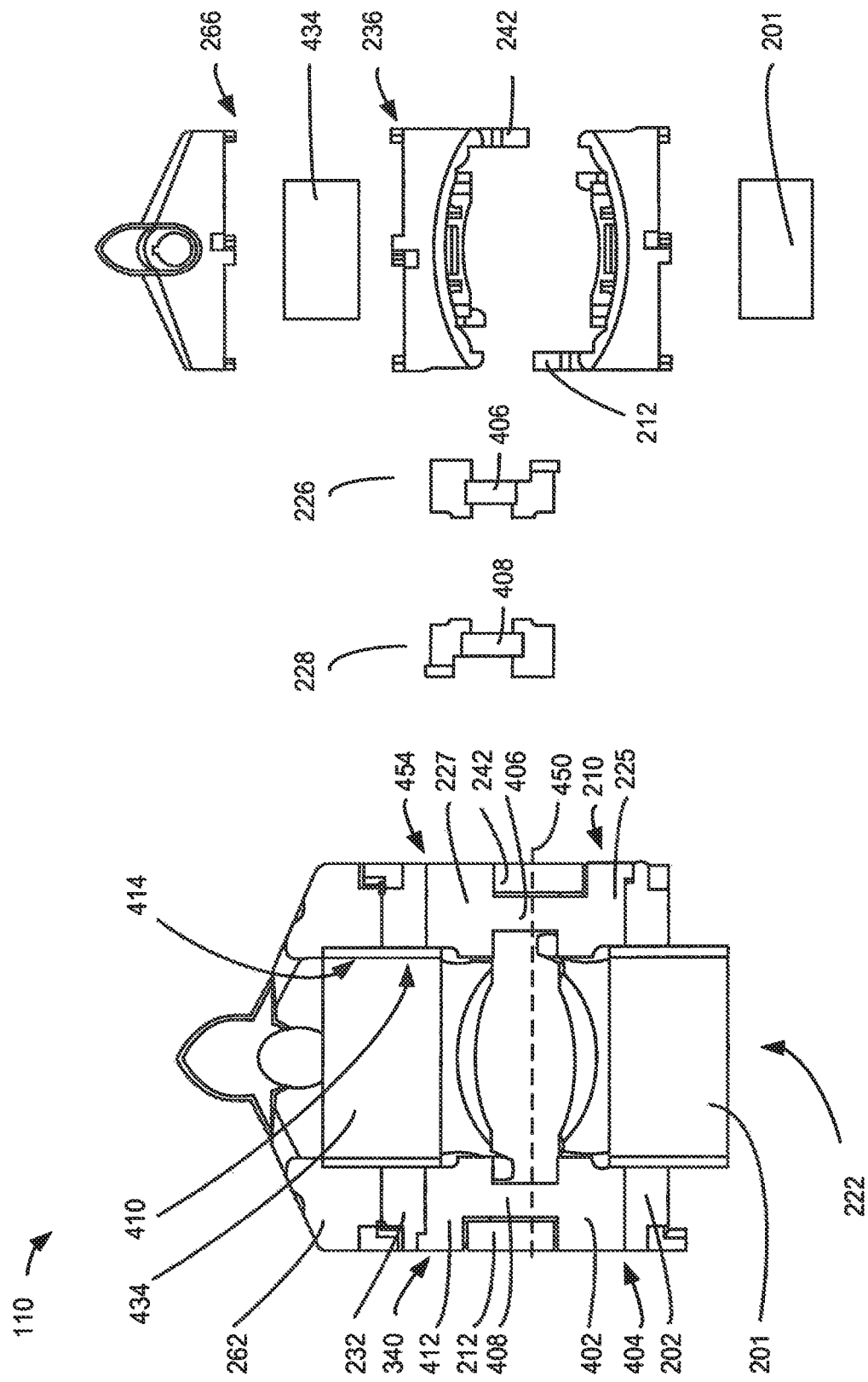
FIG. 4 is an exploded side view of the snake wrist structure in a second embodiment.

Referring now to FIG. 4 therein is shown an exploded side view of the snake wrist structure 110 in a second embodiment. The snake wrist structure 110 can include the first locking member 201 and the first joint disk 202.

The first locking member 201 can be connected to the first inner opening 222 of the first joint disk 202. The first locking member 201 is in direct contact with the first slot bearing 225 of the first strut 226 and with a second hole bearing 402 of the second strut 228. The first locking member 201 presses against and holds in place the first slot bearing 225 and the second hole bearing 402.

The first joint disk 202 is over the first locking member 201. The second joint disk 232 is mounted over the first joint disk 202.

The first joint disk 202 is connected to the second joint disk 232 with the first strut 226. The first strut 226 is adjacent to the second toothed gear 242. The first strut 226 can include the first slot bearing 225 and the first hole bearing 227 connected by the first connection link 406. The first hole bearing 227 is inserted into a second bearing hole 454. The first slot bearing 225 is inserted into the first tooth slot 210.

The second joint disk 232 is connected to the first joint disk 202 with the second strut 228. The second strut 228 is adjacent to the first toothed gear 212. The second strut 228 can include a second slot bearing 412 and the second hole bearing 402 connected by a second connection link 408. The second hole bearing 402 is inserted into the first bearing hole 404. The second slot bearing 412 is inserted into the second tooth slot 340.

A second locking element 434 is connected to a second inner opening 410 of the second joint disk 232. The second locking element 434 is in direct contact with the first hole bearing 227 of the first strut 226 and the second slot bearing 412 of the second strut 228.

The third joint disk 262 is mounted over the second joint disk 232 with the second alignment keys 236 interlocked with the third alignment keys 266. The second locking element 434 is connected to a third interior portion 414 of the third joint disk 262.

It has been discovered that the present invention provides the medical instrument 100 with improved reliability of operation. The use of the second toothed gear 242 in the first tooth slot 210 supports the maintaining of constant length cabling in the snake wrist structure 110. Constant length cabling is defined as a cabling configuration where the cables maintain a constant length. Constant length cabling can insure that as a cable is pulled out of one side of a joint, the opposite side will take up an equal amount of cable.

The first joint disk 202 and the second joint disk 232 form a joint that can flex around a flex axis 450. The flex axis 450 is defined the effective axis formed by the first strut 226 and the second strut 228 when connected between the first joint disk 202 and the second joint disk 232.

Figure 5:
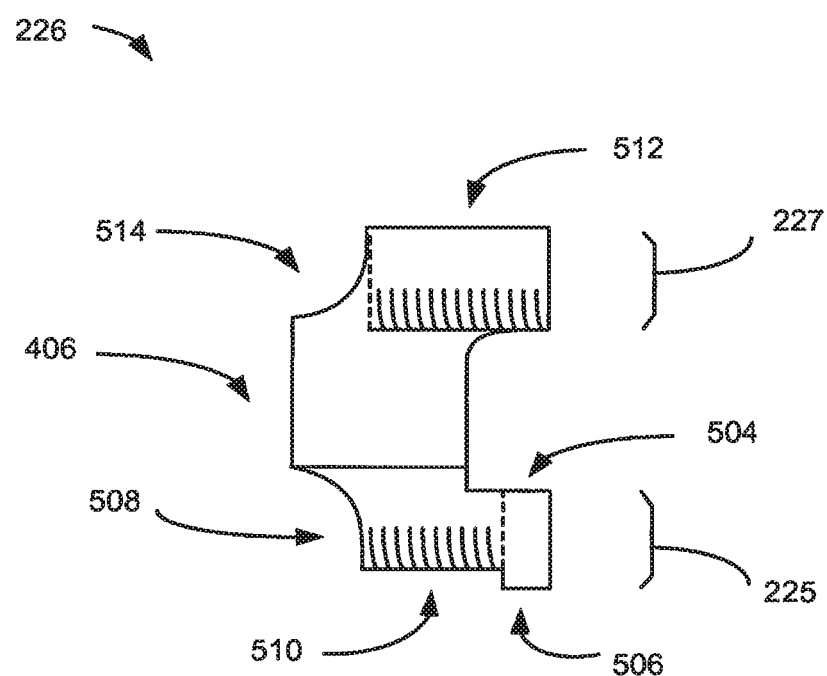
FIG. 5 is an example of the first strut in a second embodiment.

Referring now to FIG. 5, therein is shown an example of the first strut 226 in a second embodiment. The first strut 226 can include the first slot bearing 225, the first hole bearing 227, and the first connection link 406.

The first strut 226 can be a two bearing structure for connecting the first joint disk 202 of FIG. 2 and the second joint disk 232 of FIG. 2. Each bearing can form the axle for a joint disk that allows the joint disk to rotate around the bearing.

The first slot bearing 225 can be a structure forming an axle for rotation of the first joint disk 202. The first slot bearing 225 is roughly cylindrical. The first strut 226 can include a first landing surface 504 facing the first hole bearing 227. The first landing surface 504 can include a flat surface facing the first hole bearing 227.

The first slot bearing 225 can include a first locking lip 506 on the outer edge of the first slot bearing 225 on the side facing away from the first hole bearing 227. The first locking lip 506 can be a structure to prevent motion of the first slot bearing 225 by attaching to a matching hole. The first locking lip 506 can be at the outer edge of the first hole bearing 227 used to engage in a slot or edge to lock the first hole bearing 227 in place.

The first strut 226 can include a first slot locking notch 508 on the inner edge of the first slot bearing 225. The inner edge of the first slot bearing 225 is defined as the edge facing the second strut 228 of FIG. 2. The first slot bearing 225 can include a first slot bearing surface 510 on the side of the first slot bearing 225 facing away from the first hole bearing 227.

The first strut 226 can include the first connection link 406 between the first slot bearing 225 and the first hole bearing 227. The first connection link 406 is directly connected to the first slot bearing 225 and the first hole bearing 227.

The first hole bearing 227 can be a structure forming an axle for rotation of the second joint disk 232. The first hole bearing 227 is roughly cylindrical. The first strut 226 can include the first hole locking notch 514 on the inner edge of the first hole bearing 227. The inner edge of the first hole bearing 227 is the edge facing the second strut 228. The first hole bearing 227 can include a first hole bearing surface 512 on the side of the first hole bearing 227 facing away from the first slot bearing 225.

The snake wrist structure 110 can include a variety of strut configuration examples. For example, the strut can include two bearing surfaces on either end of a mechanical link. One bearing surface can connect the strut to a tooth-side bearing on a disk, the other can connect the strut to a slot-side bearing on a disk.

In another example, using two separate but identical struts can create a larger central lumen in the joint than having struts joined together. It has been discovered that the present invention provides a locking feature to prevent the struts from falling out of a joint in the event of a broken or damaged cable.

In yet another example, the bearing surface of the strut can be cantilevered whereby when assembled with a disk, a portion of the bearing surface is aligned underneath the tooth feature. It has been discovered that the this cantilevered geometry allowed for a greater through-lumen size without reducing the bearing surface area of the strut and the corresponding overall load capacity of the joint.

Figure 6:
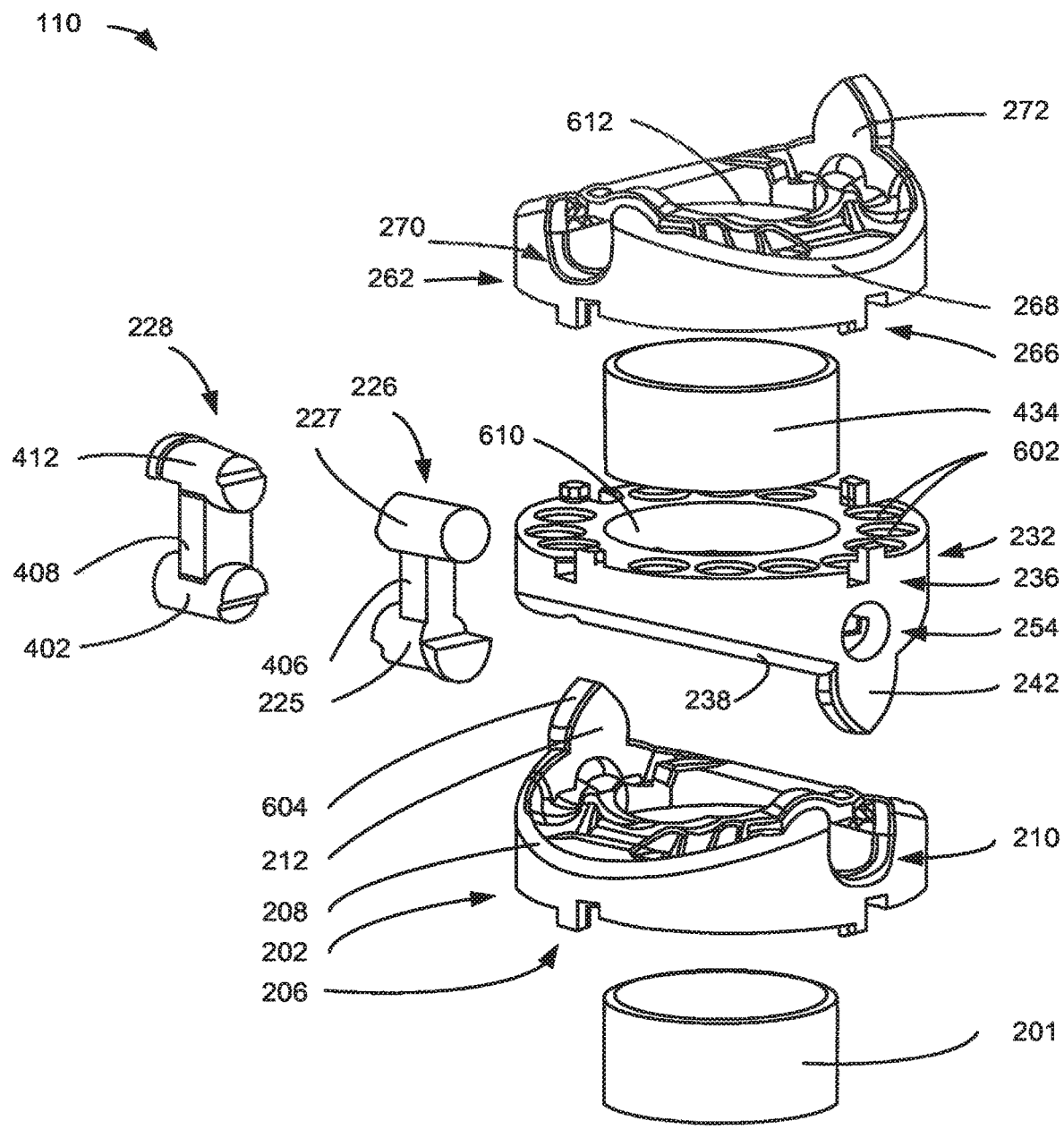
FIG. 6 is an exploded view of the snake wrist structure in a second embodiment.

Referring now to FIG. 6 therein is shown an exploded view of the snake wrist structure 110 in a second embodiment. The snake wrist structure 110 includes the first locking member 201, the first joint disk 202, the first strut 226, the second strut 228, the second joint disk 232, the second locking element 434, and the third joint disk 262.

The first joint disk 202 is over the first locking member 201. The first joint disk 202 can include the first alignment keys 206, the first angled surface 208, the first tooth slot 210, and the first toothed gear 212.

The first strut 226 can be connected between the first joint disk 202 and the second joint disk 232. The first strut 226 can include the first hole bearing 227, the first slot bearing 225, and the first connection link 406.

The second strut 228 can be connected between the first joint disk 202 and the second joint disk 232. The second strut 228 can include the second hole bearing 402, the second slot bearing 412, and the second connection link 408. The second strut 228 can have the same configuration as the first strut 226 rotated 180 degrees in the vertical direction.

The second joint disk 232 is over the first joint disk 202. The second joint disk 232 can include the second alignment keys 236, the second angled surface 238, the second toothed gear 242, the second bearing hole 254, a second inner opening 610, and a set of second cable holes 602.

The second locking element 434 is between the second joint disk 232 and the third joint disk 262. The third joint disk 262 can include the third alignment keys 266, the third angled surface 268, the third tooth slot 270, the third toothed gear 272, and a third inner opening 612. The third joint disk 262 is over the second locking element 434 and the second joint disk 232.

The first toothed gear 212 can include a first toothed gear coating 604 on the surface of the first toothed gear 212 to reduce friction between the first joint disk 202 and the second joint disk 232. The first toothed gear coating 604 is defined as a wear resistant material over the surface of the first toothed gear 212. For example, the first toothed gear 212 can be manufactured of a variety of medical grade metal alloys. The medical grade metal alloys composition can include Nitronic 60, surgical stainless steel, titanium, nickel, chromium, molybdenum, or a combination thereof. The first toothed gear 212 can include a wear-resistant coating on the tooth to prevent galling and wear. The first toothed gear coating 604 can include a variety of medical grade wear-resistant coatings such as diamond-like carbon, thin dense chromium, fluropolymer, or Medcoat 2000. The material of the first toothed gear 212 and the material of the first strut 226 can be selected as a complimentary pair for preventing galling.

It has been discovered that the present invention provides the medical instrument 100 with improved durability and wear resistance. Including a first toothed gear coating 604 on the surface of the first toothed gear 212 can prevent galling and wear on the first strut 226, leading to an extended operational life of the snake wrist structure 110. The wear-resistant coating can reduce friction between the first joint disk 202 and the second joint disk 232 resulting in less wear that can allow the use of softer materials in the manufacture of the first strut 226.

The first strut 226 includes the first slot bearing 225 and the first hole bearing 227 connected by the first connection link 406. The first strut 226 can support three axes of rotation. The first joint disk 202 can rotate around the first slot bearing 225. The second joint disk 232 can rotate around the first hole bearing 227. The first slot bearing 225 and the first hole bearing 227 can rotate relative to each other and the first connection link 406.

The first slot bearing 225 can include a first slot bearing surface 510 of FIG. 5. The first hole bearing 227 can include a first hole bearing surface 512 of FIG. 5. Because the first strut 226 has two bearings, the first slot bearing 225 and the first hole bearing 227, the first strut 226 can include a large overall bearing surface area and a higher load capacity. Thus, the first strut 226 with two bearings can be smaller than a strut with only one bearing for the same load capacity. This allows the overall physical dimensions of the first strut 226 to be reduced.

It has been discovered that the present invention provides the medical instrument 100 with a larger cable payload in the snake wrist lumen 290 because the snake wrist lumen 290 can be larger. Providing the first strut 226 with two bearings, the first slot bearing 225 and the first hole bearing 227, reduces the overall size of each bearing by 50% over that needed to support the same load with a single bearing joint. The first strut 226 can be of smaller size in terms of bearing diameter, bearing width, or a combination thereof. The smaller version of the first strut 226 can be used in the snake wrist structure 110 with a thinner first rim 209 resulting in an increased diameter of the snake wrist lumen 290. If the snake wrist lumen 290 is larger, the amount of cables and payload in the snake wrist lumen 290 can be increased to provide additional capability for the snake wrist structure 110.

The first strut 226 and the second strut 228 lock the first joint disk 202 and the second joint disk 232 together. Locking is defined as holding two elements together in the same relative position and orientation while still allowing the intended rolling motion of the joint. For example, the locking means the first joint disk 202 and the second joint disk 232 cannot shift laterally or separate axially, but are still free to pivot. The centroids of the first joint disk 202 and the second joint disk 232 maintain the same relative position with respect to each other as one disk pivots with respect to another. Locking can hold the first joint disk 202 and the second joint disk 232 in fixed relative positions to one another even in the absence of joint control cables in the first cable holes 214 of FIG. 2 and the second cable holes 602.

It has been discovered that the present invention provides the medical instrument 100 with improved physical integrity by doubling the mechanisms holding the snake wrist structure 110 together. The physical integrity of the snake wrist structure 110 is increased 100% in terms of preventing accidental disassembly and loss of components during operation. The first strut 226 locks the first joint disk 202 and the second joint disk 232 together without external connection structures, such as joint control cables or central lumen cables. Locking the first joint disk 202 and the second joint disk 232 together can prevent the loss of components of the snake wrist structure 110 in case elements such as the joint control cables are damaged or broken. Preventing the loss of components makes the snake wrist structure 110 safer by reducing the likelihood of a component being lost within a patient during surgery.

Figure 7:
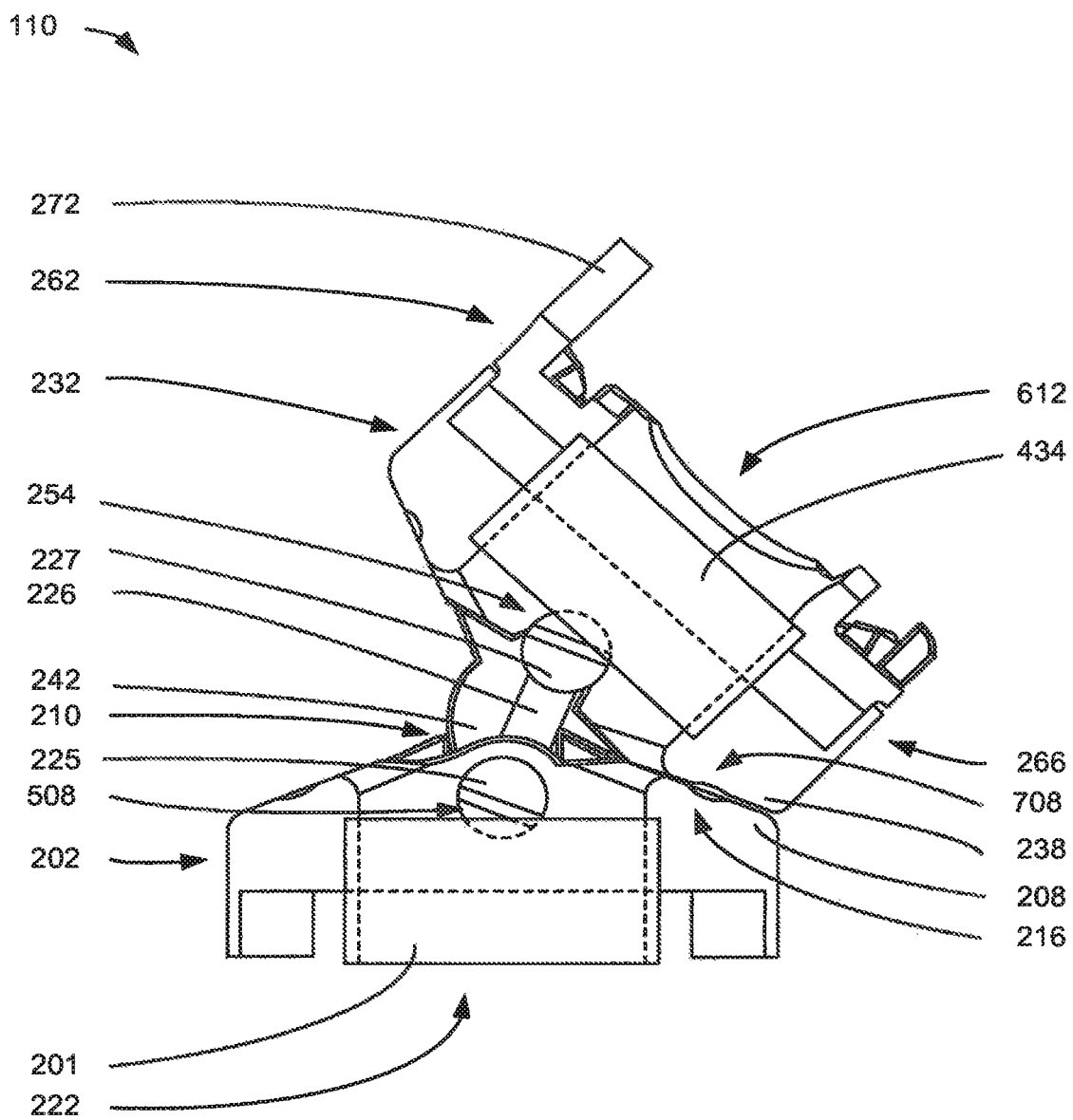
FIG. 7 is a cutaway view of the snake wrist structure in a flexed position in a second embodiment.

Referring now to FIG. 7 therein is shown a cutaway view of the snake wrist structure 110 in a flexed position in a second embodiment. The snake wrist structure 110 includes the first locking member 201, the first joint disk 202, the first strut 226, the second joint disk 232, the second locking element 434, and the third joint disk 262.

The first locking member 201 is directly connected to the first inner opening 222 of the first joint disk 202. The first joint disk 202 is over the first locking member 201.

The first joint disk 202 includes the first angled surface 208, the first bearing hole 404 and the first inner opening 222. The first strut 226 is mounted between the first joint disk 202 and the second joint disk 232. The first slot bearing 225 of the first strut 226 is mounted in the first bearing hole 404.

The first strut 226 is held in place by the first locking member 201. The first locking member 201 is in direct contact with the first slot locking notch 508 of the first slot bearing 225. The first slot bearing 225 prevents the first strut 226 from slipping into the first inner opening 222 of the first joint disk 202.

The second joint disk 232 includes the second angled surface 238, the second toothed gear 242, and the second inner opening 410 of FIG. 4. The first hole bearing 227 of the first strut 226 is inserted in the second bearing hole 254. The first angled surface 208 can include a portion that is part of the first cable cutout 216. The second angled surface 238 includes a second angled surface cutout 708.

The second joint disk 232 is shown in a flexed position with the one side of the second angled surface 238 in direct contact with the first angled surface 208 of the first joint disk 202. The second joint disk 232 can rotate around the first hole bearing 227 of the first strut 226. The first joint disk 202 can rotate around the first slot bearing 225 of the first strut 226.

The maximum degree of deflection between the first joint disk 202 and the second joint disk 232 is limited by the geometry of the first angled surface 208 and the second angled surface 238. For example, the first angled surface 208 and the second angled surface 238 are each at an angle of 22.5 degrees from the horizontal. The maximum deflection between the first joint disk 202 and the second joint disk 232 is 45 degrees.

It has been discovered that the present invention provides the medical instrument 100 with simplified manufacturing. The first angled surface 208 and the second angled surface 238 can be used to limit the degree of flex in the snake wrist structure 110 without further device or limiting mechanisms. The meeting of the first angled surface 208 and the second angled surface 238 limits the degree of flex and thus eliminates the need for external limiters, such as gear mechanisms or strut, and internal limitation features such as bumps, spacers, stoppers, tabs, or a combination thereof, and simplify manufacturing complexity and reduce manufacturing costs.

The second toothed gear 242 of the second joint disk 232 remains partially in the first tooth slot 210 of the first joint disk 202 as the snake wrist structure 110 is flexed. In the flexed position, the tip of the second toothed gear 242 is within the first tooth slot 210. As the second joint disk 232 is unflexed, the shape of the second toothed gear 242 allows the second toothed gear 242 to slide back into the first tooth slot 210 as the second joint disk 232 returns to a non-flexed position. The second toothed gear 242 and the first tooth slot 210 act together to align the first joint disk 202 and the second joint disk 232 during flexing of the snake wrist structure 110.

It has been discovered that the present invention provides the medical instrument 100 with improved reliability of operation. The position and shape of the second toothed gear 242 in the first tooth slot 210 can align the first joint disk 202 and the second joint disk 232 during the flexing of the snake wrist structure 110. When the snake wrist structure 110 is flexed or unflexed, the tip of the second toothed gear 242 is in the first tooth slot 210 and guides the second toothed gear 242 smoothly into the first tooth slot 210, preventing misalignment and dislocation of the second toothed gear 242.

The second locking element 434 is directly connected to the second inner opening of the second joint disk 232. The second locking element 434 is over the second locking element 434. The second locking element 434 is directly connected to the third interior portion 414 of the third joint disk 262.

The third joint disk 262 is over the second joint disk 232. The third joint disk 262 is directly connected the second joint disk 232 with the second alignment keys 236 of the second joint disk 232 interlocking with the third alignment keys 266 of the third joint disk 262. The third joint disk 262 includes the third toothed gear 272 and the third inner opening 612.

Figure 8:
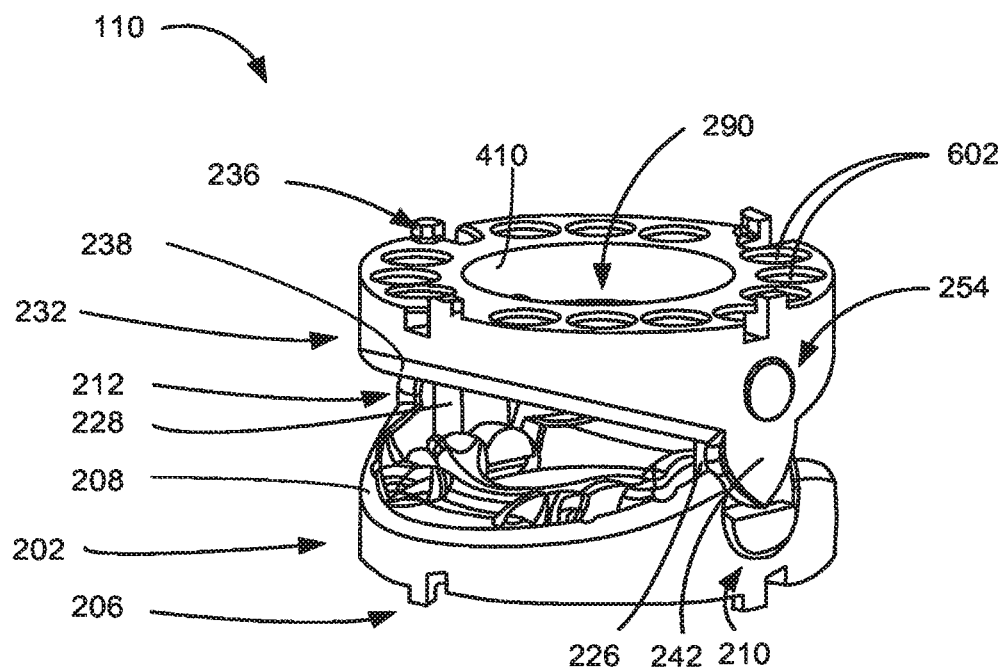
FIG. 8 is an isometric view of the snake wrist structure in an unflexed position in a second embodiment.

Referring now to FIG. 8 therein is shown an isometric view of the snake wrist structure 110 in an unflexed position in a second embodiment. The snake wrist structure 110 can include the first joint disk 202, the first strut 226, the second strut 228, the second joint disk 232, and the snake wrist lumen 290.

The first joint disk 202 can include the first alignment keys 206, the first angled surface 208, the first cable holes 214 of FIG. 2, the first cable cutouts 216 of FIG. 2, the first toothed gear 212, and the first tooth slot 210. The first joint disk 202 is below the second joint disk 232.

The first cable holes 214 are defined as opening for passing joint control cables through joint disks. The first cable holes 214 can be openings extending through the first joint disk 202 to provide access for the joint control cables (not shown). The joint control cables are defined as cables that are used to control the flexing of joints in the snake wrist structure 110.

The first cable holes 214 are adjacent to the first angled surface 208. The first joint disk 202 can include the first cable cutouts 216 around the first cable holes 214 on the same side of the first joint disk 202 as the first angled surface 208. The first cable cutouts 216 can be beveled areas around the first cable holes 214 to accommodate motion of the joint control cables when the snake wrist structure 110 is flexed. The first cable cutouts 216 are around the first cable holes 214 and can include a portion of the first angled surface 208. The first cable cutouts 216 are beveled to reduce abrasion of the joint control cables against the sides of the first cable holes 214 when the snake wrist structure 110 is flexed.

The second joint disk 232 can include the second toothed gear 242, the second bearing hole 254, the second alignment keys 236, the second cable holes 602, the second angled surface 238, and the second inner opening 410. The second joint disk 232 is over the first joint disk 202.

The second cable holes 602 provide access for the joint control cables through the second joint disk 232. The joint control cables can extend the length of the snake wrist structure 110 and run through the cables holes of each joint disk. The second cable holes 602 are aligned with the first cable holes 214 to allow the joint control cables to pass through both the first joint disk 202 and the second joint disk 232.

The first joint disk 202 and the second joint disk 232 are connected with the first strut 226 and the second strut 228. The second strut 228 is in the second bearing hole 254. The second toothed gear 242 is in the first tooth slot 210.

Figure 9:
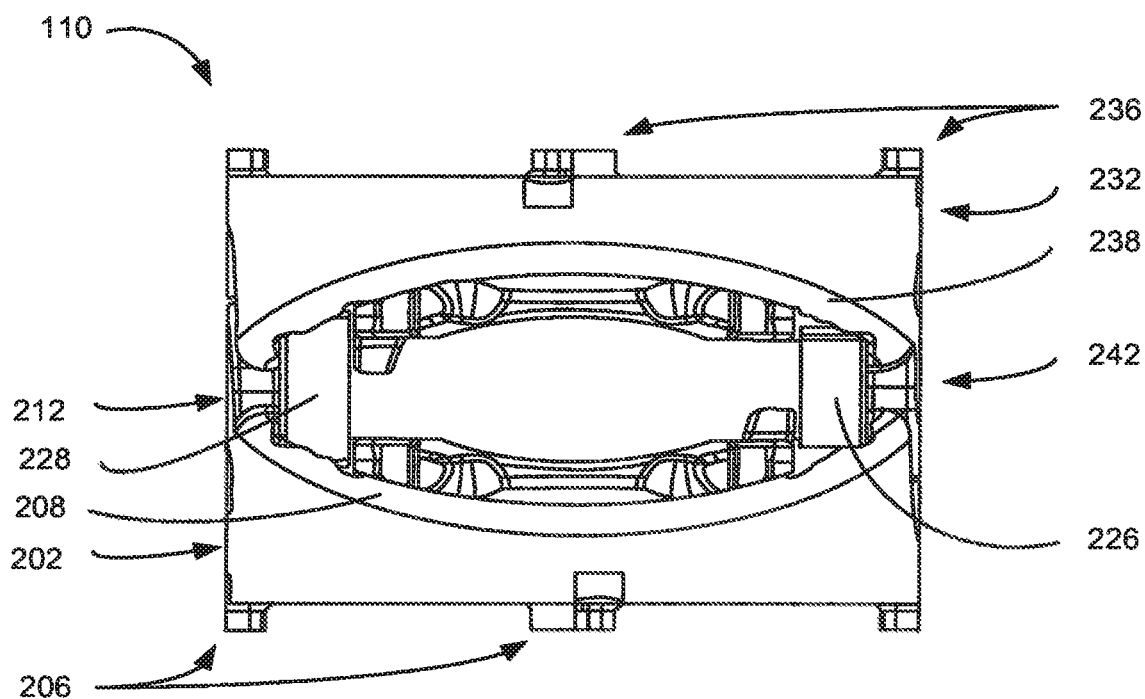
FIG. 9 is a front view of the snake wrist structure in a second embodiment.

Referring now to FIG. 9 therein is shown a front view of the snake wrist structure 110 in a second embodiment. The snake wrist structure 110 can include the first joint disk 202, the second joint disk 232, the first strut 226, and the second strut 228.

The first joint disk 202 can include the first alignment keys 206, the first angled surface 208 and the first toothed gear 212. The first joint disk 202 and the second joint disk 232 are connected with the first strut 226 and the second strut 228.

The first strut 226 is adjacent to the second toothed gear 242. The second strut 228 is adjacent to the first toothed gear 212.

The second joint disk 232 can include the second toothed gear 242, the second angled surface 238, and the second alignment keys 236. The second joint disk 232 is over the first joint disk 202.

Figure 10:
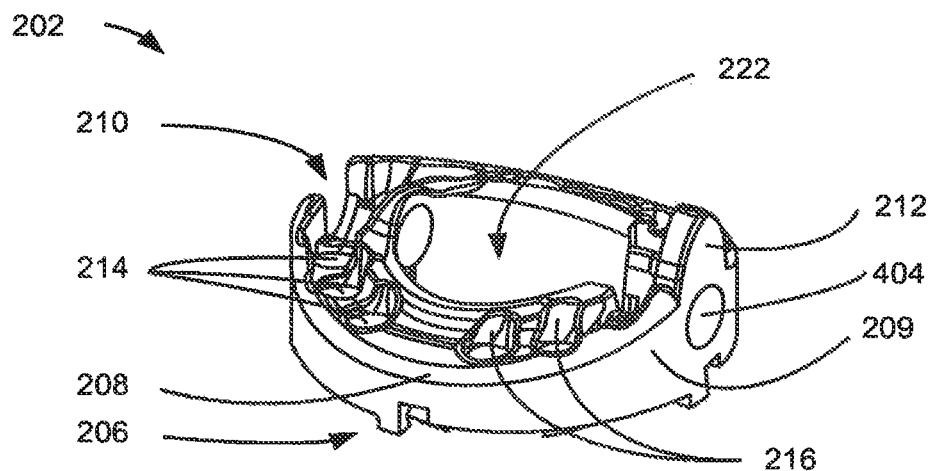
FIG. 10 is an isometric view of the first joint disk.

Referring now to FIG. 10 therein is shown an isometric view of the first joint disk 202. The first joint disk 202 can be in a variety of different embodiments. The first joint disk 202 can include the first alignment keys 206, the first angled surface 208, the first toothed gear 212, the first tooth slot 210, the first rim 209, the first inner opening 222, the first cable holes 214, and the first cable cutouts 216.

The first joint disk 202 can include the first toothed gear 212 on the first rim 209. The first bearing hole 404 is directly below the first toothed gear 212 between the first toothed gear 212 and one of the first alignment keys 206 on the bottom side of the first joint disk 202.

The first joint disk 202 can include the first tooth slot 210 on the first rim 209 opposite from the first toothed gear 212. The first joint disk 202 can include the first cable holes 214 and the first cable cutouts 216 along the first rim 209 between the first toothed gear 212 and the first tooth slot 210. The first inner opening 222 is between the first toothed gear 212 and the first tooth slot 210.

Figure 11:
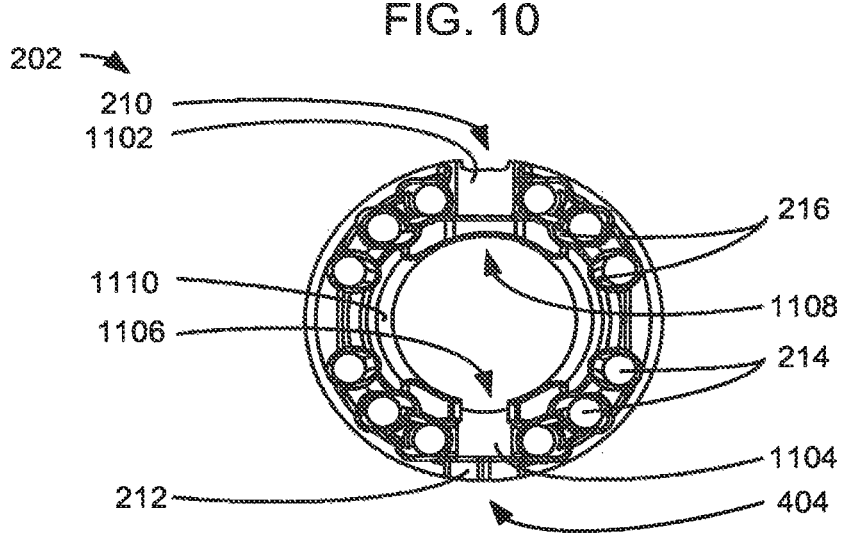
FIG. 11 is a top view of the first joint disk in a second embodiment.

Referring now to FIG. 11 therein is shown a top view of the first joint disk 202 in a second embodiment. The first joint disk 202 can include the first cable holes 214, the first cable cutouts 216, the first toothed gear 212, a first bearing mounting hole 1108, a first bearing slot 1106, and the first tooth slot 210.

The first joint disk 202 can include a first bearing bed 1102 and a second bearing bed 1104. The first bearing bed 1102 can be a surface where a bearing can be placed. The first bearing bed 1102 can be a space between the first bearing mounting hole 1108 and the first tooth slot 210. The second bearing bed 1104 can be a surface where a bearing can be placed. The second bearing bed 1104 can be a space between the first bearing slot 1106 and the first bearing hole 404.

The first bearing mounting hole 1108 is defined as a structural element for supporting the inner side of the second hole bearing 402 of FIG. 4. The first bearing mounting hole 1108 can be an hole in the first inner ring 1110. The first bearing mounting hole 1108 is adjacent to the first tooth slot 210.

The first joint disk 202 can include a first bearing slot 1106. The first bearing slot 1106 is defined as a structure that can support one side of a cylindrical bearing. The first bearing slot 1106 can be an opening in the first rim 209 of FIG. 2 of the first joint disk 202 opposite the first toothed gear 212 for accommodating the first locking lip 506 of FIG. 5 of the first strut 226 of FIG. 2.

The first joint disk 202 can include the first cable holes 214 for accommodating the joint control cables. Each joint control cable can pass through two of the first cable holes 214 on opposite sides of the flex axis 450 of FIG. 4. The first cable holes 214 can form in pairs of holes that are each equally spaced away from the flex axis 450 and on a line perpendicular to the flex axis 450 that passes through the center of the pair of holes.

Figure 12:
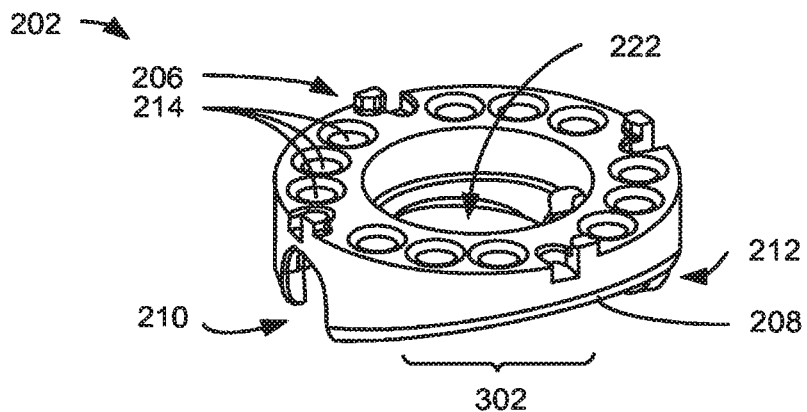
FIG. 12 is an isometric view of the bottom of the first joint disk in a second embodiment.

Referring now to FIG. 12 therein is shown an isometric view of the bottom of the first joint disk 202 in a second embodiment. The first joint disk 202 can include the first tooth slot 210, the first angled surface 208, the first cable holes 214, the first alignment keys 206, and the first inner opening 222.

The first joint disk 202 can include an interlocking structure on the bottom of the first joint disk 202 for connecting the first joint disk 202 to another element or other mounting structure. The interlocking structure can hold the first joint disk 202 and another disk element in a fixed orientation. The interlocking structure can include a variety of mating structures including the first alignment keys 206 with the first alignment key tab 203 of FIG. 2 and the first alignment key hole 205 of FIG. 2, a rib and slot structure, a pin and hole structure, a grooved structure, or a combination thereof.

For example, the first alignment keys 206 can be four interlocking structures positioned at 90 degree intervals around the bottom of the first joint disk 202. One of the first alignment keys 206 is under the first tooth slot 210. One of the first alignment keys 206 is opposite the first tooth slot 210 and under the first toothed gear 212. The other two first alignment keys 206 are under the lowest points of the first angled surface 208.

The first joint disk 202 can include the first cable holes 214 arranged around the first inner opening 222. The first cable holes 214 are arranged between the first alignment keys 206 and evenly distributed between each adjacent pair of the first alignment keys 206. The first cable holes 214 can have a beveled edge on the bottom of the first joint disk 202 to reduce cable abrasion.

The first joint disk 202 can include the first inner opening 222. The first inner opening 222 is an opening in the central portion 302 of the first joint disk 202. The first inner opening 222 can form a portion of the snake wrist lumen 290 of FIG. 2.

The snake wrist structure 110 can include a variety of joint disk configuration examples. For example, the joint disk can include two angled surfaces set at 22.5 degrees to the horizontal plane that set the range of motion limit stops for the assembled joint at .+−0.45 degrees. The joint disk can include a plurality of through-holes around the perimeter (but not present in the center plane that lies parallel to the pivot axis or the center plane perpendicular to that plane) that allow actuation cables to pass through the joint. This can include 12 holes around the perimeter but this could also be any even number of holes (2, 4, 8, 12, 16, etc. . . . ). The joint disk can include an involute "tooth" feature on one side and a corresponding "tooth-notch" on the opposite side. The joint disk can include two cylindrical concave bearing surfaces, one next-to and underneath the "tooth" feature and one next-to and underneath the "tooth-notch" feature. The joint disk can include a set of mating post and slot features on the bottom face that allow each disk to mate with the bottom face of an adjacent disk in such away that the cylindrical portions of the two disks are concentric and have a fixed orientation with respect to each other about the central axis of the disks. Also, these mating features allow the disks to be mated in fixed 90 degree increments with respect to one another. The joint disk can include surfaces and features that, when paired with mating parts, act to lock the "joint assembly" subcomponents to one another whereby they cannot be removed except by un-stacking the chain of multiple "joint assemblies" that form the instrument snake wrist.

Figure 13A:
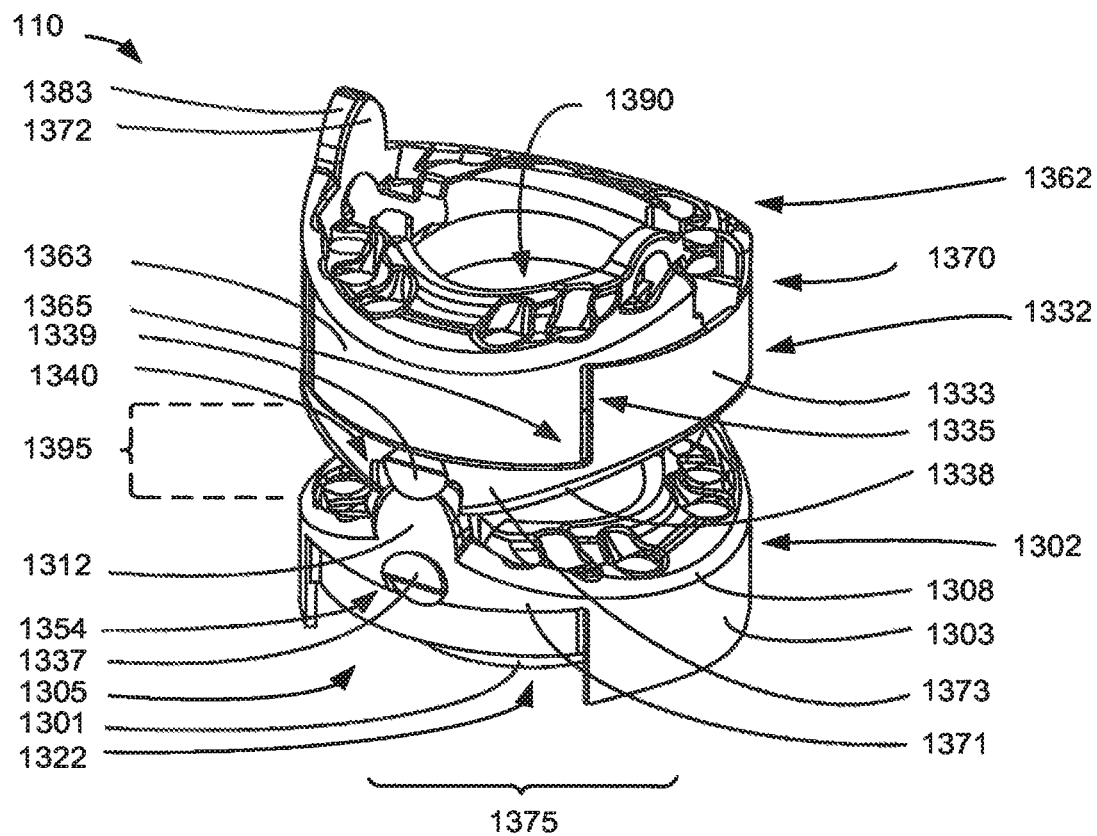
FIG. 13A is a first isometric view of the snake wrist structure in a third embodiment.

Referring now to FIG. 13A therein is shown a first isometric view of the snake wrist structure 110 in a third embodiment. The snake wrist structure 110 can include a first locking member 1301, a first joint disk 1302, a second joint disk 1332, a third joint disk 1362, and a snake wrist lumen 1390.

The snake wrist structure 110 has a first transverse dimension 1396 and a second transverse dimension 1398 along a plane orthogonal to the central axis 119 of FIG. 1. The first transverse dimension 1396 and the second transverse dimension 1398 are shown to be the same but do not need to be and may be adjusted based on the geometry of the snake wrist structure 110. In the case in which they are equal, the snake wrist structure 110 may be circular in cross section as illustrated in FIG. 2. As an example, the first transverse dimension 1396 and the second transverse dimension 1398 are shown to be along directions perpendicular to each other but does not necessarily required to be perpendicular.

The snake wrist structure 110 includes the first locking member 1301 connected to the first joint disk 1302. The first locking member 1301 can be a cylindrical tube with an outer diameter approximately equal to a diameter of a first inner opening 1322 of the first joint disk 1302. The first locking member 1301 forms a tight fit with the first inner opening 1322 when connected to the first joint disk 1302.

The first joint disk 1302 can include the first inner opening 1322. The first inner opening 1322 is defined as the central unobstructed through lumen of the first joint disk 1302. A lumen is defined as an internal cavity or opening in a cylindrical structure. The first inner opening 1322 is an opening in a central portion 1375 of the first joint disk 1302. The first inner opening 1322 can form a portion of the snake wrist lumen 1390. The central portion 1375 is defined as the interior part of the first joint disk 1302 surrounding the central axis 119 of FIG. 1.

The first joint disk 1302 can be a structural element that can be coupled to other similar disks to form the snake wrist structure 110 having the first inner opening 1322 in the center of the first joint disk 1302. The inner openings of the coupled disks of the snake wrist structure 110 form the snake wrist lumen 1390 of FIG. 13A in the snake wrist structure 110.

The snake wrist lumen 1390 is defined as a channel in the snake wrist structure 110 that can be used to pass mechanical, electrical, or optical cables or other control tubes. The snake wrist lumen 1390 can also be a through lumen for providing fluid or gas delivery or extraction, or for use as a through lumen in the instrument to allow for the passage of secondary smaller diameter surgical tools through the snake joint assembly such as a biopsy needle, grasper, or laser fiber.

The first joint disk 1302 can include a set of first alignment ribs 1303 and a set of first alignment slots 1305 around the outer diameter of the first joint disk 1302 for attaching with other joint disks. The first alignment ribs 1303 are defined as structures for connected the first joint disk 1302 to another element and for preventing rotation of the first joint disk 1302 relative to the other element. The first alignment ribs 1303 can be a portion of the outer diameter of the first joint disk 1302. The first alignment slots 1305 are defined as structures for connecting to and accommodating the first alignment ribs 1303. The first alignment slots 1305 can be the portions of the outer diameter of the first joint disk 1302 that are not the first alignment ribs 1303. The first alignment ribs 1303 and the first alignment slots 1305 are equal in size as measured around the outer diameter of the first joint disk 1302.

For example, the first joint disk 1302 can have two of the first alignment ribs 1303 and two of the first alignment slots 1305 around the outer diameter of the first joint disk 1302. The first alignment ribs 1303 and the first alignment slots 1305 can each be 25% of the outer diameter of the first joint disk 1302.

In a further example, the first alignment ribs 1303 are distributed 180 degrees apart from one another around the outer diameter of the first joint disk 1302. The first alignment ribs 1303 can be inserted in the alignment slots of another disk. The first alignment slots 1305 are distributed 180 degrees apart from on another around the outer diameter of the first joint disk 1302 and 90 degrees apart from the first alignment ribs 1303.

The first joint disk 1302 can include a first toothed gear 1312 on a first rim 1371 of the first joint disk 1302. The first toothed gear 1312 can be a single toothed gear extending from the first rim 1371 of the first joint disk 1302. The first toothed gear 1312 is centered over a first bearing hole 1354. A second hole bearing 1337 can be in the first bearing hole 1354.

The first joint disk 1302 can include a first angled surface 1308 around both sides the first rim 1371 of the first joint disk 1302 between the first toothed gear 1312 to the point on the first rim 1371 opposite the first toothed gear 1312. The first angled surface 1308 extends in downward directions from the base of the first toothed gear 1312 and the point on the first rim 1371 opposite the first toothed gear 1312 and reaches a maximum depth midway between the first toothed gear 1312 and the opposite point. The first angled surface 1308 is formed at an angle of 22.5 degrees below a plane orthogonal to the central axis 119.

The first rim 1371 is defined as a structural element around the circumference of the top of the first joint disk 1302. The first rim 1371 can include the first toothed gear 1312 and the first angled surface 1308.

The snake wrist structure 110 can include the second joint disk 1332. The second joint disk 1332 can have the same configuration as the first joint disk 1302. The second joint disk 1332 is mounted over the first joint disk 1302 in an inverted position and rotated 180 degrees.

The second joint disk 1332 can include a second tooth slot 1340, a second angled surface 1338, a set of second alignment ribs 1333, and a set of second alignment slots 1335. The first toothed gear 1312 is inserted in the second tooth slot 1340. A second slot bearing 1339 can be in the second tooth slot 1340.

The second angled surface 1338 is over the first angled surface 1308. The second angled surface 1338 faces the first angled surface 1308.

The second joint disk 1332 can include the second alignment ribs 1333 and the second alignment slots 1335 around the outer diameter of the second joint disk 1332 for attaching with other joint disks. The second alignment ribs 1333 are defined as structures for connecting the second joint disk 1332 with another joint disk in a fixed orientation and to prevent rotation of the second joint disk 1332 relative to the other joint disk. The second alignment slots 1335 are defined as the portions of the outer diameter of the second joint disk 1332 that are not the second alignment ribs 1333. The second alignment ribs 1333 and the second alignment slots 1335 are equal in size as measured around the outer diameter of the second joint disk 1332.

For example, the second joint disk 1332 can have two of the second alignment ribs 1333 and two of the second alignment slots 1335 around the outer diameter of the second joint disk 1332. The second alignment ribs 1333 and the second alignment slots 1335 can each be 25% of the outer diameter of the second joint disk 1332.

In a further example, the second alignment ribs 1333 are distributed 180 degrees apart from one another around the outer diameter of the second joint disk 1332. The second alignment ribs 1333 can be inserted in the alignment slots of another disk. The second alignment slots 1335 are distributed 180 degrees apart from on another around the outer diameter of the second joint disk 1332 and 90 degrees apart from the second alignment ribs 1333.

The second joint disk 1332 can include the second angled surface 1338 around both sides of a second rim 1373 of the second joint disk 1332. The second angled surface 1338 extends in a semicircular arc in an downward direction from the second tooth slot 1340 reaching a maximum depth midway between the second tooth slot 1340 and the point opposite the second tooth slot 1340 on the second rim 1373 of the second joint disk 1332. The second angled surface 1338 is formed an angle of 22.5 degrees below a plane orthogonal to the central axis 119.

It has been discovered that the present invention provides the medical instrument 100 with simplified manufacturing. The first angled surface 1308 and the second angled surface 1338 can be used to limit the degree of flex in the snake wrist structure 110 without further device or limiting mechanisms. The meeting of the first angled surface 1308 and the second angled surface 1338 limits the degree of flex and thus eliminates the need for external limiters, such as gear mechanisms or strut, and internal limitation features such as bumps, spacers, stoppers, tabs, or a combination thereof, and simplify manufacturing complexity and reduce manufacturing costs.

The snake wrist structure 110 can include the third joint disk 1362. The third joint disk 1362 can have the same configuration as the first joint disk 1302 and the second joint disk 1332. The third joint disk 1362 is mounted over and directly in contact with the second joint disk 1332.

The third joint disk 1362 can include a set of third alignment ribs 1363 and a set of third alignment slots 1365 around the outer diameter of the third joint disk 1362 for attaching with other joint disks. The third alignment ribs 1363 are defined as structures for connecting the third joint disk 1362 with another joint disk in a fixed orientation and to prevent rotation of the third joint disk 1362 relative to the other joint disk. The third alignment slots 1365 are defined as the portions of the outer diameter of the third joint disk 1362 that are not the third alignment ribs 1363. The third alignment ribs 1363 and the third alignment slots 1365 are equal in size as measured around the outer diameter of the third joint disk 1362.

For example, the third joint disk 1362 can have two of the third alignment ribs 1363 and two of the third alignment slots 1365 around the outer diameter of the third joint disk 1362. The third alignment ribs 1363 and the third alignment slots 1365 can each be 25% of the outer diameter of the third joint disk 1362.

In a further example, the third alignment ribs 1363 are distributed 180 degrees apart from one another around the outer diameter of the third joint disk 1362. The third alignment ribs 1363 can be inserted in the alignment slots of another disk. The third alignment slots 1365 are distributed 180 degrees apart from on another around the outer diameter of the third joint disk 1362 and 90 degrees apart from the third alignment ribs 1363.

The third joint disk 1362 can include a third tooth slot 1370 and a third toothed gear 1372. The third joint disk 1362 can be mounted over the second joint disk 1332 whereby the third tooth slot 1370 and the third toothed gear 1372 are rotated 90 degrees away from the second tooth slot 1340. The third tooth slot 1370 and the third toothed gear 1372 are on the opposite side of the third joint disk 1362 from the second joint disk 1332.

The first toothed gear 1312 can include a first toothed gear coating 1383 on the surface of the first toothed gear 1312 to reduce friction between the first joint disk 1302 and the second joint disk 1332. The first toothed gear coating 1382 is defined as a wear resistant material over the surface of the first toothed gear 1312. For example, the first toothed gear 1312 can be manufactured of a variety of medical grade metal alloys. The medical grade metal alloys composition can include Nitronic 60, surgical stainless steel, titanium, nickel, chromium, molybdenum, or a combination thereof. The first toothed gear 1312 can include a wear-resistant coating on the tooth to prevent galling and wear. The first toothed gear coating 1383 can include a variety of medical grade wear-resistant coatings such as diamond-like carbon, thin dense chromium, fluropolymer, or Medcoat 2000.

It has been discovered that the present invention provides the medical instrument 100 with improved durability and wear resistance. Including a first toothed gear coating 1383 on the surface of the first toothed gear 1312 can prevent galling and wear on the first strut 1526, leading to an extended operational life of the snake wrist structure 110. The wear-resistant coating can reduce friction between the first joint disk 1302 and the second joint disk 1332 resulting in less wear that can allow the use of softer materials in the manufacture of the first strut 1526.

The snake wrist structure 110 can flex in a variety of ways with different degrees of freedom. For example, when the second joint disk 1332 is flexed toward one side of the snake wrist structure 110, the angular degree of flex is limited by the geometry of the first angled surface 1308 and the second angled surface 1338. The second joint disk 1332 can only flex a maximum of 45 degrees if when the first angled surface 1308 and the second angled surface 1338 each form a 22.5 degree angle from the horizontal plane. The range of motion of the second joint disk 1332 is limited by when the first angled surface 1308 and the second angled surface 1338 meet and prevent further motion.

The first joint disk 1302, the second joint disk 1332, and the third joint disk 1362 can all have the same configuration. For example, the second joint disk 1332 and the third joint disk 1362 can be identical versions of the first joint disk 1302.

It has been discovered that having the first joint disk 1302 and the second joint disk 1332 with the same configuration can simplify the manufacture of the snake wrist structure 110 by reducing the number of unique parts required for assembly. Reducing the number of parts can simplify manufacturing complexity and reduce manufacturing cost.

The snake wrist structure 110 can include a joint knuckle 1395. The joint knuckle 1395 is formed by connecting the first joint disk 1302 to the second joint disk. The joint knuckle 1395 can have an interconnect structure on the proximal and distal ends to facilitate connecting to a further member such as a joint knuckle, instrument, mounting member, or a combination thereof.

Figure 13B:
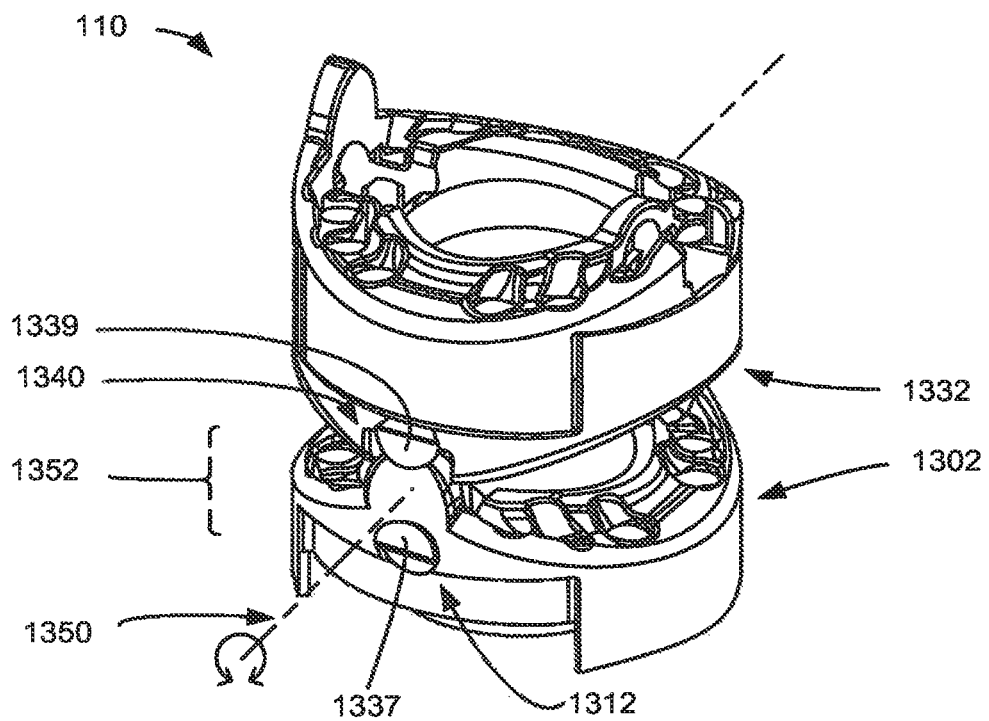
FIG. 13B is a second isometric view of the snake wrist structure in a third embodiment.

Referring now to FIG. 13B therein is shown a second isometric view of the snake wrist structure 110 in a third embodiment. The snake wrist structure 110 can include the first joint disk 1302, the second joint disk 1332, and a flex axis 1350.

The first joint disk 1302 and the second joint disk 1332 form a joint that can flex around the flex axis 1350. The flex axis 1350 is defined as the effective axis between the first joint disk 1302 and the second joint disk 1332.

The first toothed gear 1312 and the second tooth slot 1340 form a rolling joint 1352 between the first joint disk 1302 and the second joint disk 1332. The rolling joint 1352 is defined as a structure that forms a multi-axis joint between two elements having multiple degrees of freedom. The rolling joint 1352 can be the structure where the first joint disk 1302 and the second joint disk 1332 join to creates a rolling motion whereby the path of the second joint disk 1332 with respect to first joint disk 1302 is defined as the same path as that of the centroid of one circle rolling on the circumference of an identical circle where each circle has a diameter equal to the distance between the second slot bearing 1339 and the second hole bearing 1337.

As the snake wrist structure 110 is flexed, the second joint disk 1332 pivots around the first toothed gear 1312 in the second tooth slot 1340. The first toothed gear 1312 coupled with the second tooth slot 1340 provide a constraint with an involute profile on the shape of the first toothed gear 1312 enforcing the rolling motion of the joint. The involute profile of the tooth is defined by the path traced by a point on the circumference of a circle rolling on an identical circle where each circle has a diameter equal to the distance between the second slot bearing 1339 and the second hole bearing 1337.

Figure 14:
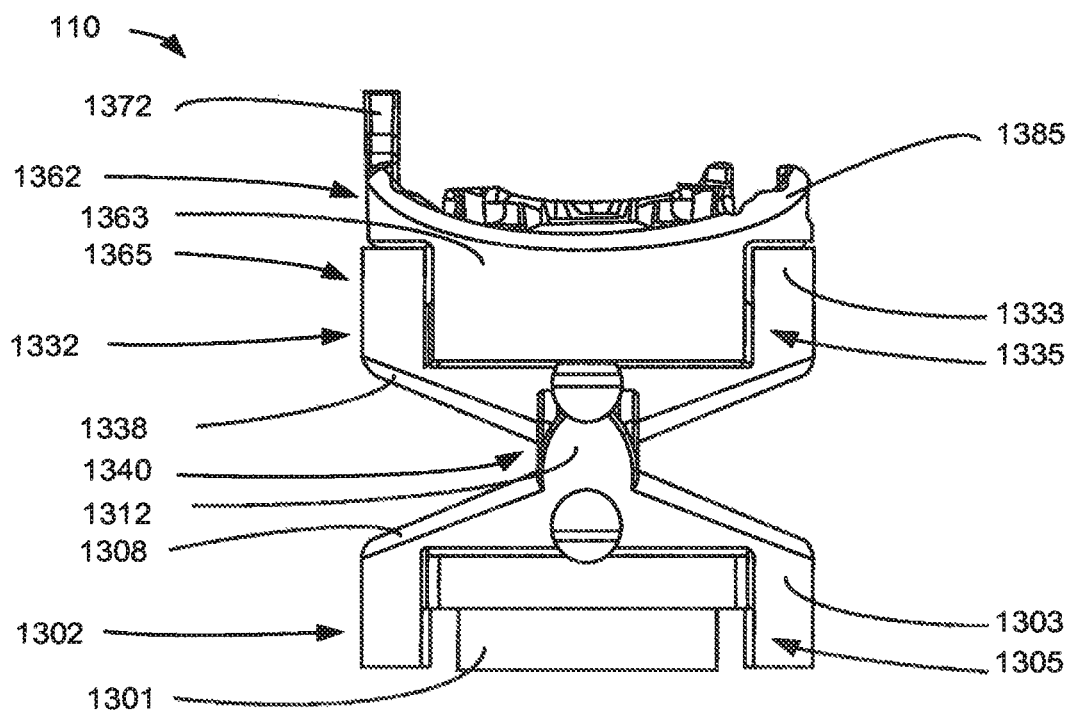
FIG. 14 is a side view of the snake wrist structure in an unflexed position in a third embodiment.

Referring now to FIG. 14 therein is shown a side view of the snake wrist structure 110 in an unflexed position in a third embodiment. The snake wrist structure 110 can include the first locking member 1301, the first joint disk 1302, the second joint disk 1332, and the third joint disk 1362.

The first locking member 1301 is connected to the first joint disk 1302. The first joint disk 1302 is over the first locking member 1301.

The first joint disk 1302 can include the first alignment ribs 1303, the first alignment slots 1305, the first angled surface 1308, and the first toothed gear 1312.

The second joint disk 1332 can include the second angled surface 1338, the second tooth slot 1340, the second alignment ribs 1333, and the second alignment slots 1335. The second joint disk 1332 is over the first joint disk 1302.

The third joint disk 1362 can include the third alignment ribs 1363, the third alignment slots 1365, the third toothed gear 1372, and a third angled surface 1385. The third joint disk 1362 is over the second joint disk 1332.

The third joint disk 1362 is rotated whereby the third alignment ribs 1363 are directly over the second alignment slots 1335. The third joint disk 1362 is directly connected to the second joint disk 1332. The third alignment ribs 1363 are in direct contact with the second alignment slots 1335 to connect the second joint disk 1332 and the third joint disk 1362.

For example, the third joint disk 1362 can be rotated 90 degrees around the central axis 119 of FIG. 13A and mounted on the second joint disk 1332. By mounting the third joint disk 1362 at a 90 degree angle to the second joint disk 1332, the snake wrist structure 110 can flex orthogonally to the flex axis 1350 of FIG. 13A of the first joint disk 1302 and the second joint disk 1332.

In another example, the third joint disk 1362 can be rotated 180 degrees around the central axis 119 and mounted on the second joint disk 1332. By mounting the third joint disk 1362 at a 180 degree angle to the second joint disk 1332, the snake wrist structure 110 can flex further around the flex axis 1350.

Figure 15:
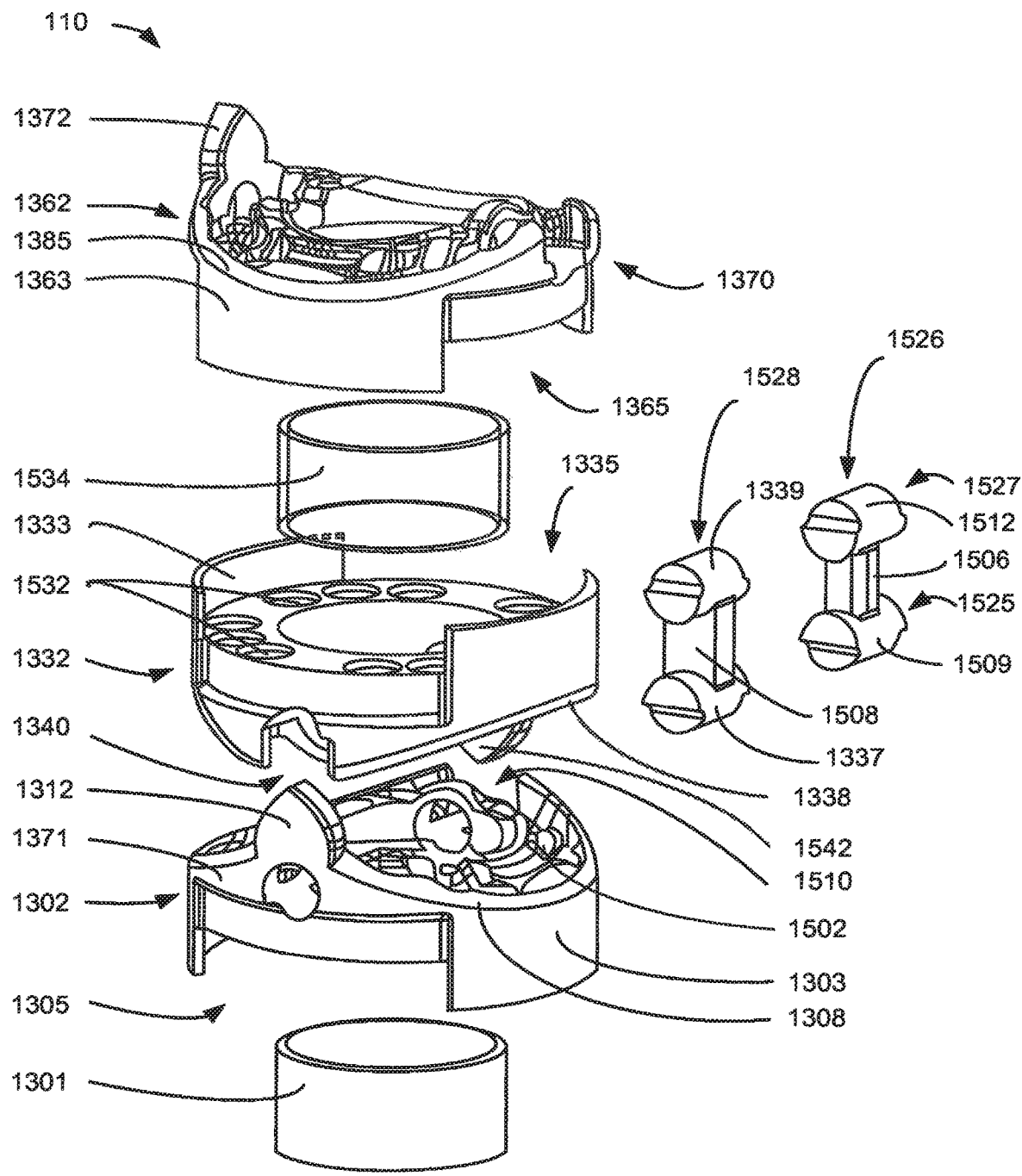
FIG. 15 is an exploded view of the snake wrist structure in a third embodiment.

Referring now to FIG. 15 therein is shown an exploded view of the snake wrist structure 110 in a third embodiment. The snake wrist structure 110 includes the first locking member 1301, the first joint disk 1302, the second joint disk 1332, a first strut 1526, a second strut 1528, a second locking element 1534, and the third joint disk 1362.

The first joint disk 1302 is over the first locking member 1301. The first joint disk 1302 can include the first alignment ribs 1303, the first alignment slots 1305, the first angled surface 1308, a first tooth slot 1510, the first toothed gear 1312 and the first cable holes 1502.

The first joint disk 1302 can include a first tooth slot 1510 on the first rim 1371 of the first joint disk 1302. The first tooth slot 1510 can be a concave opening in the first rim 1371 of the first joint disk 1302.

The second joint disk 1332 is over the first joint disk 1302. The second joint disk 1332 can include the second alignment ribs 1333, the second alignment slots 1335, the second angled surface 1338, the second tooth slot 1340, a second toothed gear 1542, and a set of second cable holes 1532.

The first strut 1526 can be connected between the first joint disk 1302 and the second joint disk 1332. The first strut 1526 can include the first hole bearing 1527, the first slot bearing 1525, and the first connection link 1506.

The second strut 1528 can be connected between the first joint disk 1302 and the second joint disk 1332. The second strut 1528 can include the second hole bearing 1337, the second slot bearing 1339, and a second connection link 1508. The second strut 1528 can have the same configuration as the first strut 1526 rotated 180 degrees in the vertical direction.

The second locking element 1534 is between the second joint disk 1332 and the third joint disk 1362. The third joint disk 1362 is over the second locking element 1534 and the second joint disk 1332. The third joint disk 1362 can include the third alignment ribs 1363, the third alignment slots 1365, the third angled surface 1385, the third tooth slot 1370, and the third toothed gear 1372.

The first strut 1526 includes the first slot bearing 1525 and the first hole bearing 1527 connected by the first connection link 1506. The first strut 1526 can support three axes of rotation. The first joint disk 1302 can rotate around the first slot bearing 1525. The second joint disk 1332 can rotate around the first hole bearing 1527. The first slot bearing 1525 and the first hole bearing 1527 can rotate relative to each other and the first connection link 1506.

The first slot bearing 1525 can include a first slot bearing surface 1509. The first hole bearing 1527 can include a first hole bearing surface 1512. Because the first strut 1526 has two bearings, the first slot bearing 1525 and the first hole bearing 1527, the first strut 1526 can include a large overall bearing surface area and a higher load capacity. Thus, the first strut 1526 with two bearings can be smaller than a strut with only one bearing for the same load capacity. This allows the overall physical dimensions of the first strut 1526 to be reduced.

It has been discovered that the present invention provides the medical instrument 100 with a larger cable payload in the snake wrist lumen 1390 because the snake wrist lumen 1390 can be larger. Providing the first strut 1526 with two bearings, the first slot bearing 1525 and the first hole bearing 1527, reduces the overall size of each bearing by 50% over that needed to support the same load with a single bearing joint. The first strut 1526 can be of smaller size in terms of bearing diameter, bearing width, or a combination thereof. The smaller version of the first strut 1526 can be used in the snake wrist structure 110 with a thinner first rim 1371 resulting in an increased diameter of the snake wrist lumen 1390. If the snake wrist lumen 1390 is larger, the amount of cables and payload in the snake wrist lumen 1390 can be increased to provide additional capability for the snake wrist structure 110.

The first strut 1526 and the second strut 1528 can lock the first joint disk 1302 and the second joint disk 1332 together. Locking is defined as holding two elements together in the same relative position and orientation while still allowing the intended rolling motion of the joint. For example, the locking means the first joint disk 1302 and the second joint disk 1332 cannot shift laterally or separate axially, but are still free to pivot. The centroids of the first joint disk 1302 and the second joint disk 1332 maintain the same relative position with respect to each other as one disk pivots with respect to another. Locking can hold the first joint disk 1302 and the second joint disk 1332 in fixed relative positions to one another even in the absence or failure of joint control cables.

It has been discovered that the present invention provides the medical instrument 100 with improved physical integrity by doubling the mechanisms holding the snake wrist structure 110 together. The physical integrity of the snake wrist structure 110 is increased 100% in terms of preventing accidental disassembly and loss of components during operation. The first strut 1526 locks the first joint disk 1302 and the second joint disk 1332 together without external connection structures, such as joint control cables or central lumen cables. Locking the first joint disk 1302 and the second joint disk 1332 together can prevent the loss of components of the snake wrist structure 110 in case elements such as the joint control cables are damaged or broken. Preventing the loss of components makes the snake wrist structure 110 safer by reducing the likelihood of a component being lost within a patient during surgery.

It has also been discovered that the present invention provides the medical instrument 100 with improved reliability of operation. The use of the second toothed gear 1542 in the first tooth slot 1510 supports the maintaining of constant length cabling in the snake wrist structure 110. Constant length cabling can be achieved by insuring that as a cable is pulled out of one side of a joint, the side opposite cable will take up an equal length of cable.

The second toothed gear 1542 of the second joint disk 1332 remains partially in the first tooth slot 1510 of the first joint disk 1302 as the snake wrist structure 110 is flexed. In the flexed position, the tip of the second toothed gear 1542 is within the first tooth slot 1510. As the second joint disk 1332 is unflexed, the shape of the second toothed gear 1542 allows the second toothed gear 1542 to slide back into the first tooth slot 1510 as the second joint disk 1332 returns to a non-flexed position. The second toothed gear 1542 and the first tooth slot 1510 act together to align the first joint disk 1302 and the second joint disk 1332 during flexing of the snake wrist structure 110.

It has been discovered that the present invention provides the medical instrument 100 with improved reliability of operation. The position and shape of the second toothed gear 1542 in the first tooth slot 1510 can align the first joint disk 1302 and the second joint disk 1332 during the flexing of the snake wrist structure 110. When the snake wrist structure 110 is flexed or unflexed, the tip of the second toothed gear 1542 is in the first tooth slot 1510 and guides the second toothed gear 1542 smoothly into the first tooth slot 1510, preventing misalignment and dislocation of the second toothed gear 1542.

Figure 16:
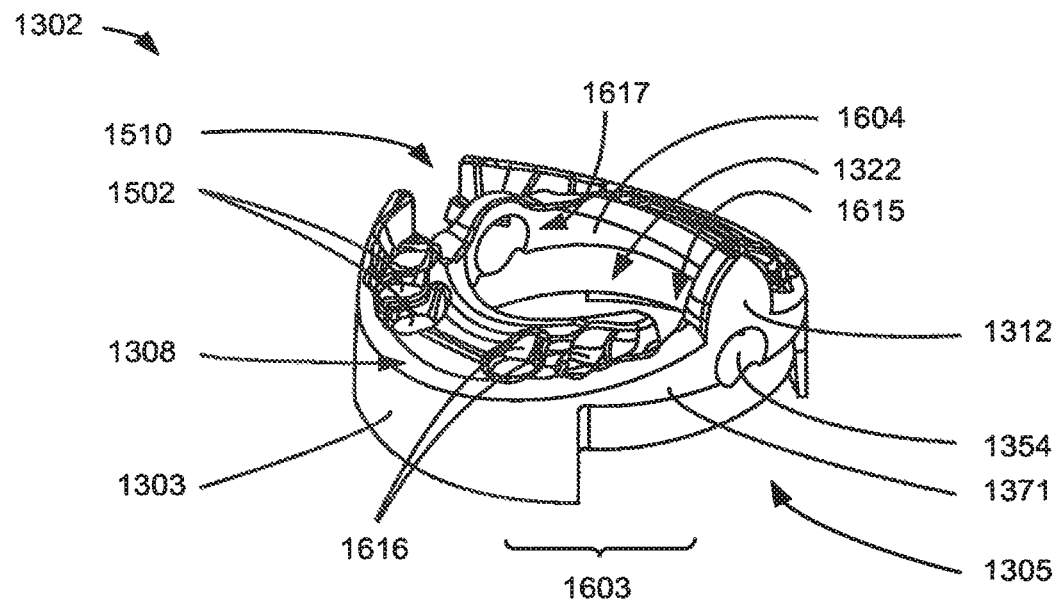
FIG. 16 is an isometric view of the first joint disk in a third embodiment.

Referring now to FIG. 16 therein is shown an isometric view of the first joint disk 1302 in a third embodiment. The first joint disk 1302 can include the first alignment ribs 1303, the first alignment slots 1305, the first angled surface 1308, the first toothed gear 1312, the first tooth slot 1510, the first inner opening 1322, the first cable holes 1502, and the first cable cutouts 1616. The first joint disk 1302 can include a first rim 1371, the first inner ring 1604, the first bearing hole 1354, the first bearing slot 1615, the first bearing mounting hole 1617.

For example, the first alignment ribs 1303 and the first alignment slots 1305 are on the circumference of the bottom side of the first joint disk 1302. The first alignment ribs 1303 can each extend 25% of the circumference of the first joint disk 1302. The first alignment slots 1305 can each extend 25% of the circumference of the first joint disk 1302. A portion of the first bearing hole 1354 can extend into the first alignment slots 1305.

The first joint disk 1302 can include the first toothed gear 1312 on the first rim 1371. The first bearing hole 1354 is directly below the first toothed gear 1312.

The first joint disk 1302 can include the first tooth slot 1510 on the first rim 1371 opposite from the first toothed gear 1312. The first joint disk 1302 can include the first bearing mounting hole 1617 on the first inner ring 1604 on the same side as the first tooth slot 1510.

The first joint disk 1302 can include the first cable holes 1502 and the first cable cutouts 1616 between the first rim 1371 and the first inner ring 1604. The first inner ring 1604 is around the first inner opening 1322. The first inner opening 1322 is between the first bearing slot 1615 and the first bearing mounting hole 1617.

The first joint disk 1302 can include the first inner opening 1322. The first inner opening 1322 is an opening in a central portion 1603 of the first joint disk 1302.

Figure 17:
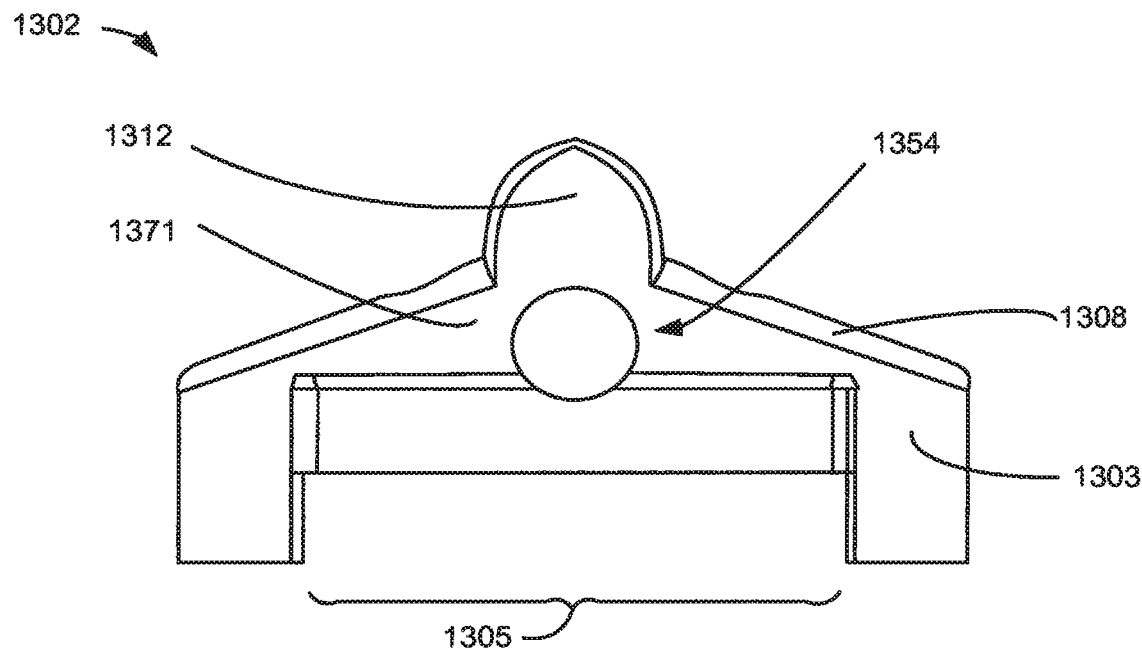
FIG. 17 is a side view of the bottom of the first joint disk in a third embodiment.

Referring now to FIG. 17 therein is shown a side view of the first joint disk 1302 in a third embodiment. The first joint disk 1302 can include the first alignment ribs 1303, the first alignment slots 1305, the first angled surface 1308, the first toothed gear 1312, and the first bearing hole 1354.

For example, the first alignment ribs 1303 and the first alignment slots 1305 are on the circumference of the bottom side of the first joint disk 1302. The first alignment ribs 1303 can each extend 25% of the circumference of the first joint disk 1302. The first alignment slots 1305 can each extend 25% of the circumference of the first joint disk 1302. A portion of the first bearing hole 1354 can extend into the first alignment slots 1305.

The first joint disk 1302 can include the first toothed gear 1312 on the first rim 1371. The first bearing hole 1354 is directly below the first toothed gear 1312 between the first toothed gear 1312 and one of the first alignment slots 1305 on the bottom side of the first joint disk 1302.

Figure 18:
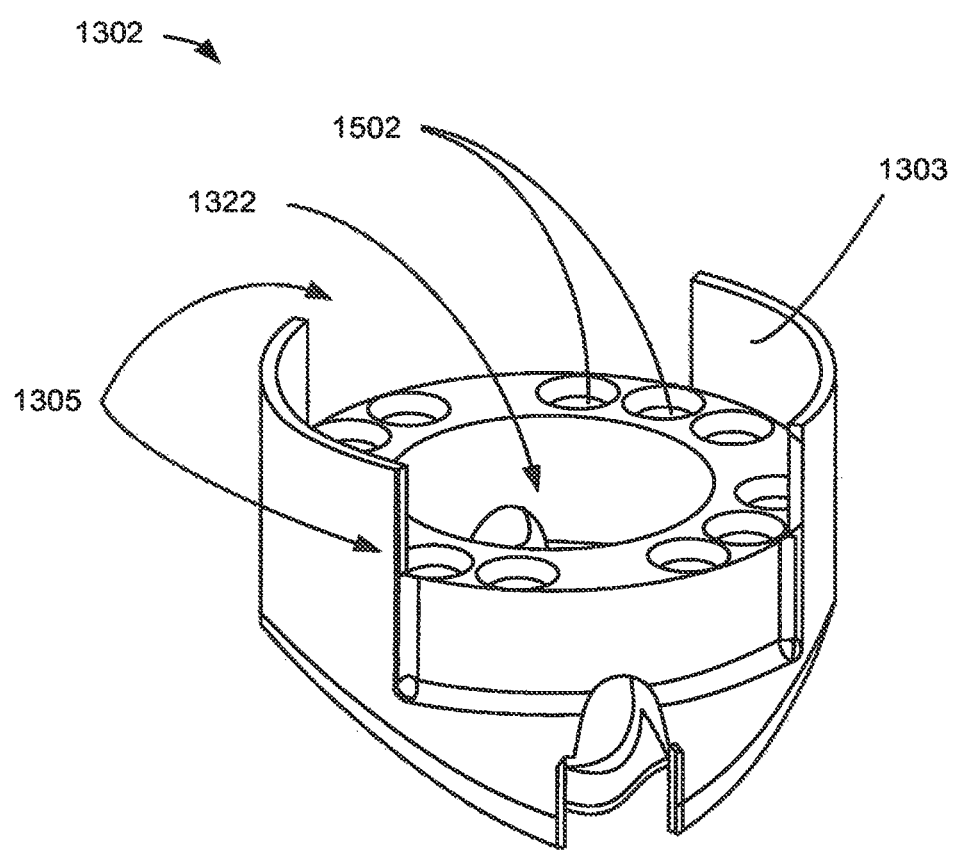
FIG. 18 is an isometric view of the bottom of the first joint disk in a third embodiment.

Referring now to FIG. 18 therein is shown an isometric view of the bottom of the first joint disk 1302 in a third embodiment. The first joint disk 1302 can include the first cable holes 1502, the first alignment ribs 1303, the first alignment slots 1305, and the first inner opening 1322.

The first joint disk 1302 can include an interlocking structure for connecting the first joint disk 1302 to another disk element or other mounting structure. The interlocking structure can hold the first joint disk 1302 and another disk element in a fixed orientation. The interlocking structure can include a variety of mating structures including the first alignment ribs 1303 and the first alignment slots 1305, an alignment hole, a tab and hole structure, a pin and hole structure, a grooved structure, or a combination thereof.

For example, the first alignment ribs 1303 and the first alignment slots 1305 are on the circumference of the first joint disk 1302. A portion of the first tooth slot 1510 can extent into one of the first alignment slots 1305.

The first joint disk 1302 can include the first cable holes 1502 arranged around the first inner opening 1322. The first cable holes 1502 can have a beveled edge on the bottom of the first joint disk 1302.

Figure 19A:
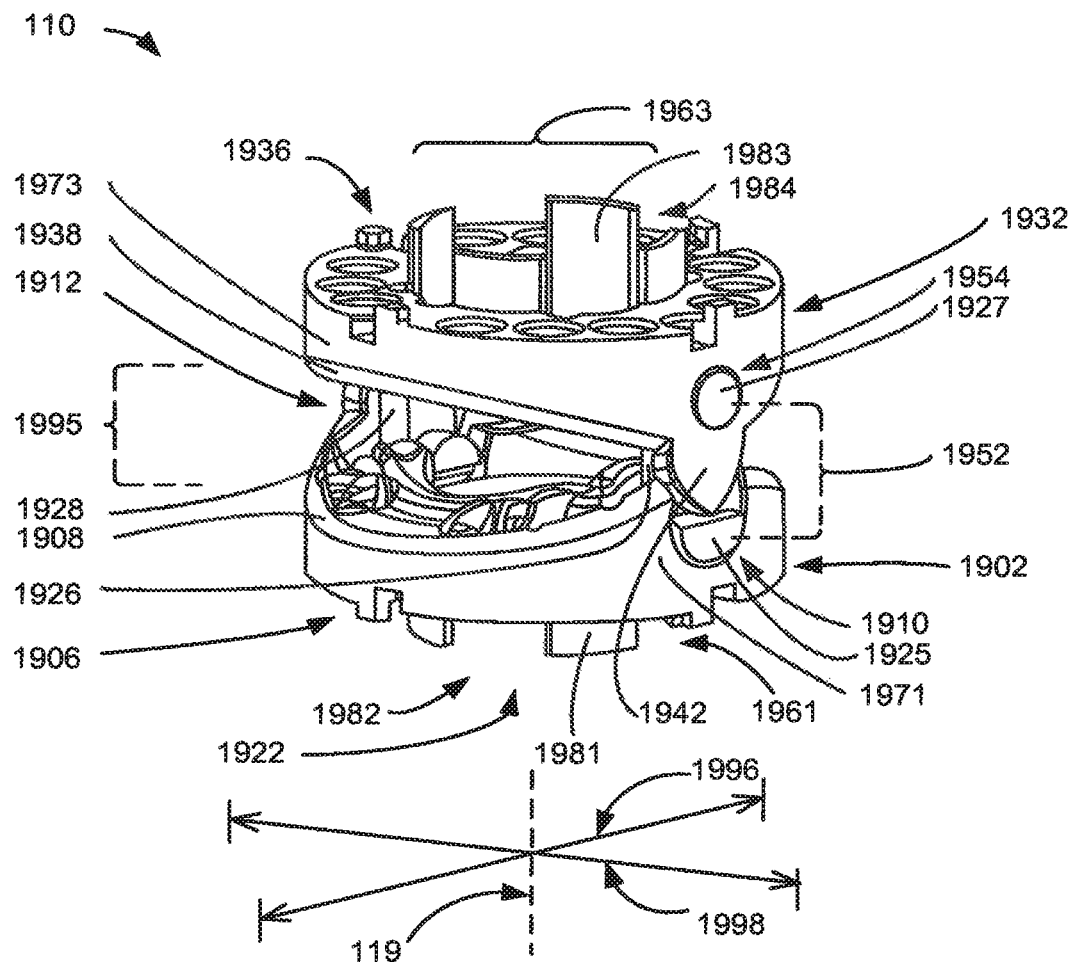
FIG. 19A is a first isometric view of the snake wrist structure in a fourth embodiment.

Referring now to FIG. 19A, therein is shown a first isometric view of the snake wrist structure 110 in a fourth embodiment. The snake wrist structure 110 can include a first joint disk 1902, a second joint disk 1932, and a first inner interlock structure 1961.

The snake wrist structure 110 can include the first inner interlock structure 1961 around the inside diameter of the first inner opening 1922. The first inner interlock structure 1961 can include first interlock ribs 1981 and first interlock slots 1982 extending below the bottom of the first joint disk 1902.

The snake wrist structure 110 can include a second inner interlock structure 1963. The second inner interlock structure 1963 can include a set of second interlock ribs 1983 and a set of second interlock slots 1984 extending below the bottom of the second joint disk 1932.

For example, the first inner interlock structure 1961 can be used to attach to another disk element or to a mounting structure. The first interlock ribs 1981 can connect to the complementary interlock slots of another element to hold the first joint disk 1902 in a fixed orientation to the other disk element or mounting structure.

The first joint disk 1902 has first alignment keys 1906 around the bottom of the circumference of the first joint disk 1902. The first alignment keys 1906 are distributed 90 degrees apart from one another around the bottom circumference of the first joint disk 1902. The first alignment keys 1906 are defined as structures for connecting the first joint disk 1902 with another disk in a fixed orientation and to prevent rotation of the first joint disk 1902 relative to another disk.

The first joint disk 1902 can include a first tooth slot 1910 on a first rim 1971 of the first joint disk 1902. The first tooth slot 1910 can be a concave opening in the first rim 1971 of the first joint disk 1902.

The first joint disk 1902 can include a first toothed gear 1912 on the opposite side of the first rim 1971 across from the first tooth slot 1910. The first toothed gear 1912 can be a single toothed gear extending from the first rim 1971 of the first joint disk 1902.

The first joint disk 1902 can include a first angled surface 1908 around both sides the first rim 1971 of the first joint disk 1902 between the first toothed gear 1912 to the first tooth slot 1910. The first angled surface 1908 extends in downward directions from the base of the first toothed gear 1912 and top of the first tooth slot 1910 reaching a maximum depth midway between the first toothed gear 1912 and the first tooth slot 1910. The first angled surface 1908 is formed an angle of 22.5 degrees below a plane orthogonal to the central axis 119 of FIG. 1.

The first rim 1971 is defined as a structural element around the circumference of the top of the first joint disk 1902. The first rim 1971 can include the first tooth slot 1910 and the first angled surface 1908.

The snake wrist structure 110 can include the second joint disk 1932. The second joint disk 1932 can have the same configuration as the first joint disk 1902. The second joint disk 1932 is mounted over the first joint disk 1902 in an inverted position and rotated 180 degrees.

The second joint disk 1932 can include a second toothed gear 1942. The second joint disk 1932 is mounted over the first joint disk 1902 whereby the second toothed gear 1942 is over the first tooth slot 1910 of the first joint disk 1902. The second toothed gear 1942 can be inserted into the first tooth slot 1910 of the first joint disk 1902.

The second joint disk 1932 can include a set of second alignment keys 1936. The second alignment keys 1936 are on the side of the second joint disk 1932 opposite from the second toothed gear 1942.

The second joint disk 1932 can include a second angled surface 1938 around both sides of a second rim 1973 of the second joint disk 1932 between the second toothed gear 1942 and a point opposite the second toothed gear 1942. The second angled surface 1938 extends in a semi-circular arc in an downward direction from the base of the second toothed gear 1942 and the point opposite the second toothed gear 1942 reaching a maximum height midway between the second toothed gear 1942 and a point opposite the second toothed gear 1942. The second angled surface 1938 is formed at an angle of 22.5 degrees below a plane orthogonal to the central axis 119.

The snake wrist structure 110 can include a joint knuckle 1995. The joint knuckle 1995 is formed by connecting the first joint disk 1902 to the second joint disk. The joint knuckle 1995 can have an interconnect structure on the proximal and distal ends to facilitate connecting to a further member such as a joint knuckle, instrument, mounting member, or a combination thereof.

The snake wrist structure 110 has a first transverse dimension 1996 and a second transverse dimension 1998 along a plane orthogonal to the central axis 119 of FIG. 1. The first transverse dimension 1996 and the second transverse dimension 1998 are shown to be the same but do not need to be and may be adjusted based on the geometry of the snake wrist structure 110. In the case in which they are equal, the snake wrist structure 110 may be circular in cross section as illustrated in FIG. 19A. As an example, the first transverse dimension 1996 and the second transverse dimension 1998 are shown to be along directions perpendicular to each other but does not necessarily required to be perpendicular.

It has been discovered that the first angled surface 1908 and the second angled surface 1938 can be used to limit the degree of flex in the snake wrist structure 110 without further device or limiting mechanism. The angle formed by the first angled surface 1908 and the second angled surface 1938 thus eliminates external limiters, such as gear mechanisms or strut, and internal limitation features such as bumps, spacers, stoppers, tabs, or a combination thereof, and simplify manufacturing complexity and reduce manufacturing costs.

The second joint disk 1932 can be coupled to the first joint disk 1902 by a first strut 1926 and a second strut 1928. The first strut 1926 can be a connecting joint structure having a first hole bearing 1927 and a first slot bearing 1925. The first strut 1926 can attach to the second joint disk 1932 with the first hole bearing 1927 inserted into a second bearing hole 1954. The first strut 1926 can attach to the first joint disk 1902 with the first slot bearing 1925 inserted into the first tooth slot 1910.

The second toothed gear 1942 of the second joint disk 1932 remains partially in the first tooth slot 1910 of the first joint disk 1902 as the snake wrist structure 110 is flexed. In the flexed position, the tip of the second toothed gear 1942 is within the first tooth slot 1910. As the second joint disk 1932 is unflexed, the shape of the second toothed gear 1942 allows the second toothed gear 1942 to slide back into the first tooth slot 1910 as the second joint disk 1932 returns to a non-flexed position. The second toothed gear 1942 and the first tooth slot 1910 act together to align the first joint disk 1902 and the second joint disk 1932 during flexing of the snake wrist structure 110.

It has been discovered that the position and shape of the second toothed gear 1942 in the first tooth slot 1910 can align the first joint disk 1902 and the second joint disk 1932 during the flexing of the snake wrist structure 110 and reduce the forces on the first strut 1926. When the stress on the first strut 1926 is reduced, it can prevent the first strut 1926 from and causing excessive friction and wear of the first strut 1926.

The snake wrist structure 110 can flex in a variety of ways with different degrees of freedom. For example, when the second joint disk 1932 is flexed toward one side of the snake wrist structure 110, the angular degree of flex is limited by the geometry of the first angled surface 1908 and the second angled surface 1938. The second joint disk 1932 can only flex a maximum of 45 degrees if when the first angled surface 1908 and the second angled surface 1938 each form a 22.5 degree angle from the horizontal plane. The range of motion of the second joint disk 1932 is limited by when the first angled surface 1908 and the second angled surface 1938 meet and prevent further motion.

The first joint disk 1902 and the second joint disk 1932 can all have the same configuration. For example, the second joint disk 1932 can be identical versions of the first joint disk 1902.

It has been discovered that having the first joint disk 1902 and the second joint disk 1932 with the same configuration can simplify the manufacture of the snake wrist structure 110 by reducing the number of unique parts required for assembly. Reducing the number of parts can simplify manufacturing complexity and reduce manufacturing cost.

The second toothed gear 1942 and the first tooth slot 1910 form a rolling joint 1952 between the first joint disk 1902 and the second joint disk 1932. The rolling joint 1952 is defined as a structure that forms a multi-axis joint between two elements having multiple degrees of freedom. The rolling joint 1952 can be the structure where the first joint disk 1902 and the second joint disk 1932 join to create a rolling motion where the path of the second joint disk 1932 with respect to first joint disk 1902 is defined as the same path as that of the centroid of one circle rolling on the circumference of an identical circle where each circle has a diameter equal to the distance between the first slot bearing 1925 and the first hole bearing 1927.

As the snake wrist structure 110 is flexed, the second joint disk 1932 pivots around the second toothed gear 1942 and the first tooth slot 1910. The second toothed gear 1942 couples with the first tooth slot 1910 to provide a constraint with an involute profile on the shape of the second toothed gear 1942 enforcing the rolling motion of the joint. The involute profile of the tooth is defined by the path traced by a point on the circumference of a circle rolling on an identical circle where each circle has a diameter equal to the distance between the first slot bearing 1925 and the first hole bearing 1927.

The first strut 1926 and the second strut 1928 lock the first joint disk 1902 and the second joint disk 1932 together. Locking is defined as holding two elements together in the same relative position and orientation while still allowing the intended rolling motion of the joint. For example, the locking means the first joint disk 1902 and the second joint disk 1932 cannot shift laterally or separate axially, but are still free to pivot. The centroids of the first joint disk 1902 and the second joint disk 1932 maintain the same relative position with respect to each other as one disk pivots with respect to another. Locking can hold the first joint disk 1902 and the second joint disk 1932 in fixed relative positions to one another even in the absence or failure of joint control cables.

It has been discovered that the present invention provides the medical instrument 100 with improved physical integrity by doubling the mechanisms holding the snake wrist structure 110 together. The physical integrity of the snake wrist structure 110 is increased 100% in terms of preventing accidental disassembly and loss of components during operation. The first strut 1926 locks the first joint disk 1902 and the second joint disk 1932 together without external connection structures, such as joint control cables or central lumen cables. Locking the first joint disk 1902 and the second joint disk 1932 together can prevent the loss of components of the snake wrist structure 110 in case elements such as the joint control cables are damaged or broken. Preventing the loss of components makes the snake wrist structure 110 safer by reducing the likelihood of a component being lost within a patient during surgery.

It has been discovered that the present invention provides the medical instrument 100 with improved reliability of operation. The use of the second toothed gear 1942 in the first tooth slot 1910 supports the maintaining of constant length cabling in the snake wrist structure 110. Constant length cabling is defined as a cabling configuration where the cables maintain a constant length. Constant length cabling can insure that as a cable is pulled out of one side of a joint, the opposite side will take up an equal amount of cable.

Figure 19B:
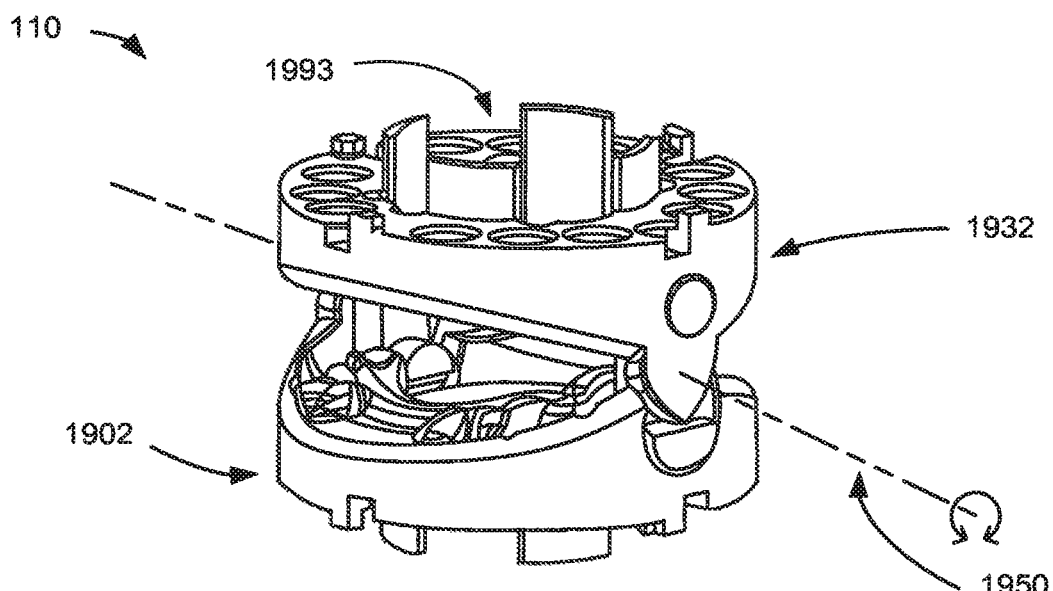
FIG. 19B is a second isometric view of the snake wrist structure in a fourth embodiment.

Referring now to FIG. 19B, therein is shown a second isometric view of the snake wrist structure 110 in a fourth embodiment. The snake wrist structure 110 can include the first joint disk 1902, the second joint disk 1932, a flex axis 1950, and a snake wrist lumen 1993.

The first joint disk 1902 and the second joint disk 1932 form a joint that can flex around the flex axis 1950. The flex axis 1950 is defined as the effective axis as the first joint disk 1902 and the second joint disk 1932 rotate around the connection formed by the first strut 1926 and the second strut 1928.

The first joint disk 1902 can be a joint structure element that can be coupled to other similar disks to form the snake wrist structure 110 having a first inner opening 1922 in the center of the first joint disk 1902. The first inner opening 1922 is defined as the central unobstructed through lumen of the first joint disk 1902. A lumen is defined as an internal cavity or opening in a cylindrical structure. The inner openings of the coupled disks of the snake wrist structure 110 form the snake wrist lumen 1993 in the snake wrist structure 110.

The snake wrist lumen 1993 is defined as a channel in the snake wrist structure 110 that can be used to pass mechanical, electrical, or optical cables or other control tubes. The snake wrist lumen 1993 can also be a through lumen for providing fluid or gas delivery or extraction, or for use as a through lumen in the instrument to allow for the passage of secondary smaller diameter surgical tools through the snake joint assembly such as a biopsy needle, grasper, or laser fiber.

Figure 20:
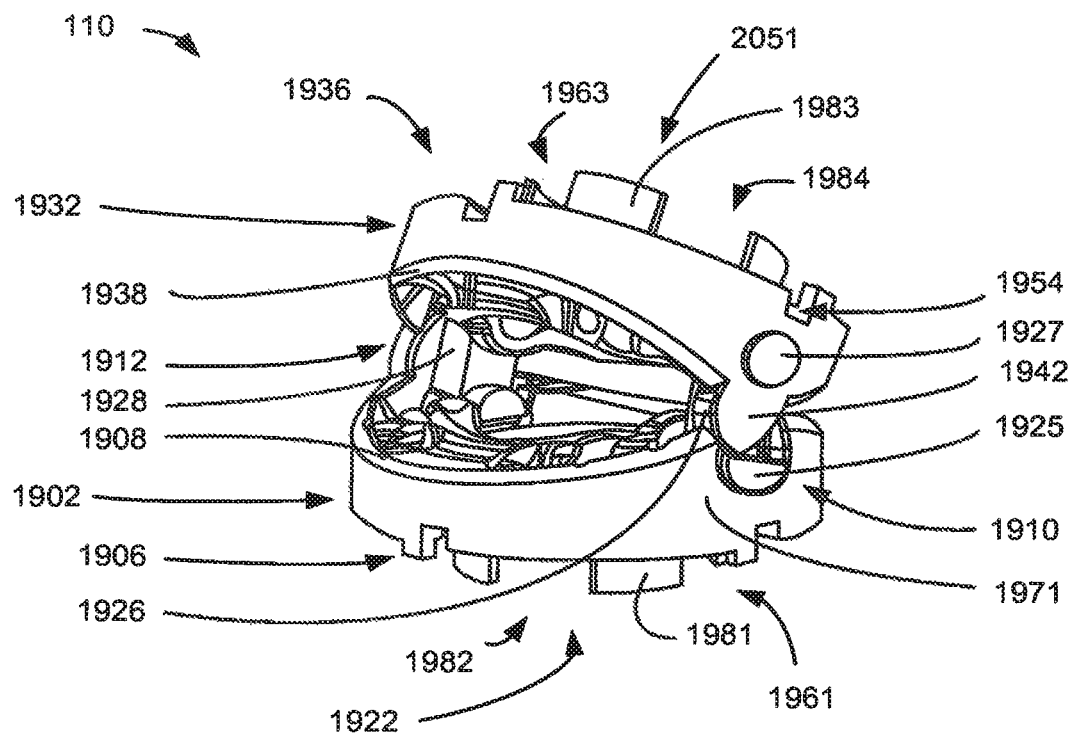
FIG. 20 is an isometric view of the snake wrist structure in a flexed position in a fourth embodiment.

Referring now to FIG. 20 therein is shown an isometric of the snake wrist structure 110 in a flexed position in a fourth embodiment. The snake wrist structure 110 can include the first joint disk 1902, the second joint disk 1932, the first inner interlock structure 1961, and the second inner interlock structure 1963.

The snake wrist structure 110 can include the first inner interlock structure 1961 around the inside diameter of the first inner opening 1922. The first inner interlock structure 1961 can include first interlock ribs 1981 and first interlock slots 1982 extending below the bottom of the first joint disk 1902.

The snake wrist structure 110 can include the second inner interlock structure 1963 around the inside diameter of a second inner opening 2051. The second inner interlock structure 1963 can include a set of second interlock ribs 1983 and a set of second interlock slots 1984 extending below the bottom of the second joint disk 1932.

The first joint disk 1902 has first alignment keys 1906 around the bottom of the circumference of the first joint disk 1902. The first alignment keys 1906 are distributed 90 degrees apart from one another around the bottom circumference of the first joint disk 1902. The first alignment keys 1906 can be connected to the alignment keys of another disk The first joint disk 1902 can include the first tooth slot 1910 on the first rim 1971 of the first joint disk 1902. The first joint disk 1902 can include the first toothed gear 1912 on the opposite side of the first rim 1971 across from the first tooth slot 1910.

The first joint disk 1902 can include the first angled surface 1908 around both sides the first rim 1971 of the first joint disk 1902 between the first toothed gear 1912 to the first tooth slot 1910. The first angled surface 1908 extends in downward directions from the base of the first toothed gear 1912 and top of the first tooth slot 1910 reaching a maximum depth midway between the first toothed gear 1912 and the first tooth slot 1910. The first angled surface 1908 is formed an angle of 22.5 degrees below a plane orthogonal to the central axis 119.

The snake wrist structure 110 can include the second joint disk 1932. The second joint disk 1932 can have the same configuration as the first joint disk 1902. The second joint disk 1932 is mounted over the first joint disk 1902 in an inverted position and rotated 180 degrees.

The second joint disk 1932 can include the second toothed gear 1942. The second joint disk 1932 is mounted over the first joint disk 1902 whereby the second toothed gear 1942 is over the first tooth slot 1910 of the first joint disk 1902. The second toothed gear 1942 can be inserted into the first tooth slot 1910 of the first joint disk 1902.

The second joint disk 1932 can include the second alignment keys 1936. The second alignment keys 1936 are on the side of the second joint disk 1932 opposite from the second toothed gear 1942 and facing away from the first joint disk 1902.

The second joint disk 1932 can include the second angled surface 1938 around both sides of the second rim 1973 of FIG. 19A of the second joint disk 1932 between the second toothed gear 1942 to point opposite the second toothed gear 1942. The second angled surface 1938 extends in a semi-circular arc in an downward direction from the base of the second toothed gear 1942 reaching a maximum height midway between the second toothed gear 1942 and a point opposite from the second toothed gear 1942. The second angled surface 1938 is formed an angle of 22.5 degrees below a plane orthogonal to the central axis 119 of FIG. 1.

The second joint disk 1932 can be coupled to the first joint disk 1902 by a first strut 1926 and the second strut 1928. The first strut 1926 can be a connecting joint structure having a first hole bearing 1927 and a first slot bearing 1925.

The first strut 1926 can attach to the second joint disk 1932 with the first hole bearing 1927 inserted into the second bearing hole 1954. The first strut 1926 can attach to the first joint disk 1902 with the first slot bearing 1925 inserted into the first tooth slot 1910.

The second joint disk 1932 can include the second alignment keys 1936 around the bottom of the circumference of the second joint disk 1932. For example, the second alignment keys 1936 are distributed 90 degrees apart from one another around the bottom circumference of the first joint disk 1902. The first alignment keys 1906 can be connected to the alignment keys of another element.

The second joint disk 1932 can be in a flexed position where the second joint disk 1932 is flexed around the bearing axis and the second angled surface 1938 is closer to the first angled surface 1908 on one side of the snake wrist structure 110 and further apart on the opposite side of the snake wrist structure 110.

Figure 21:
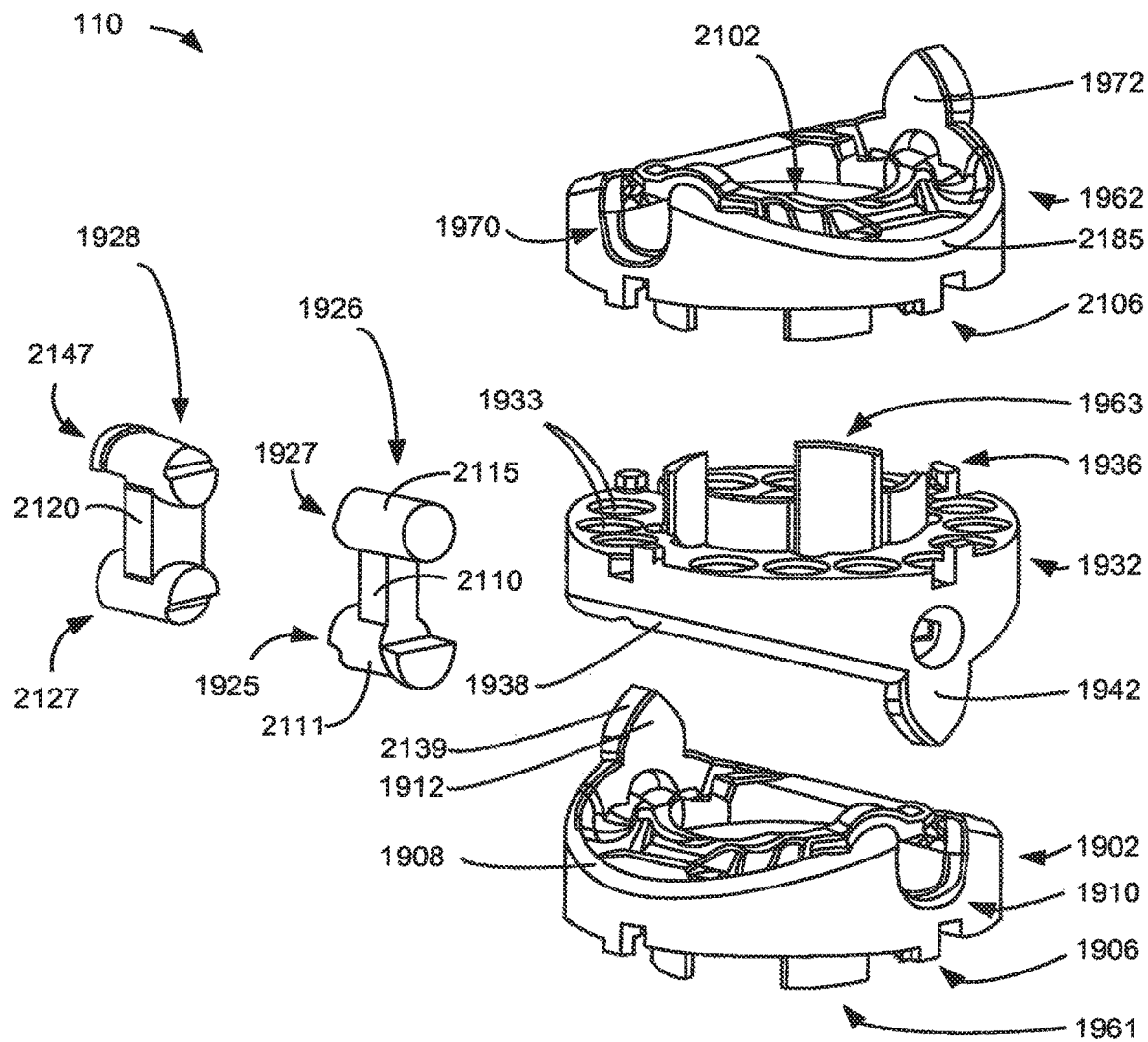
FIG. 21 is an exploded view of the snake wrist structure in a fourth embodiment.

Referring now to FIG. 21 therein is shown an exploded view of the snake wrist structure in a fourth embodiment. The snake wrist structure 110 includes a first joint disk 1902, the second joint disk 1932, a first strut 1926, the second strut 1928, a third joint disk, a first inner interlock structure 1961, the second inner interlock structure 1963, the snake wrist lumen 1993 of FIG. 19B, and a third inner interlock structure 2102.

The first joint disk 1902 can include the first alignment keys 1906, the first angled surface 1908, the first tooth slot 1910, and the first toothed gear 1912. The first joint disk 1902 can include the first inner interlock structure 1961.

The second joint disk 1932 is over the first joint disk 1902. The second joint disk 1932 can include the second alignment keys 1936, the second angled surface 1938, the second toothed gear 1942, and a set of second cable holes 1933. The second joint disk 1932 can include the second inner interlock structure 1963.

The first strut 1926 can be connected between the first joint disk 1902 and the second joint disk 1932. The first strut 1926 can include the first hole bearing 1927, the first slot bearing 1925, and the first connection link 2110.

The second strut 1928 can be connected between the first joint disk 1902 and the second joint disk 1932. The second strut 1928 can include a second hole bearing 2127, a second slot bearing 2147, and a second connection link 2120. The second strut 1928 can have the same configuration as the first strut 1926 rotated 180 degrees in the vertical direction.

A third joint disk 1962 is over the second joint disk 1932. The third joint disk 1962 can include a set of third alignment keys 2106, a third angled surface 2185, a third tooth slot 1970, a third toothed gear 1972. The third joint disk 1962 can include the third inner interlock structure 2102.

The first strut 1926 includes the first slot bearing 1925 and the first hole bearing 1927 connected by the first connection link 2110. The first strut 1926 can support three axes of rotation. The first joint disk 1902 can rotate around the first slot bearing 1925. The second joint disk 1932 can rotate around the first hole bearing 1927. The first slot bearing

1925 and the first hole bearing 1927 can rotate relative to each other and the first connection link 2110.

The first slot bearing 1925 can include a first slot bearing surface 2111. The first hole bearing 1927 can include a first hole bearing surface 2115. Because the first strut 1926 has two bearings, the first slot bearing 1925 and the first hole bearing 1927, the first strut 1926 can include a large overall bearing surface area and a higher load capacity. Thus, the first strut 1926 with two bearings can be smaller than a strut with only one bearing for the same load capacity. This allows the overall physical dimensions of the first strut 1926 to be reduced.

It has been discovered that the present invention provides the medical instrument 100 with a larger cable payload in the snake wrist lumen 1993 because the snake wrist lumen 1993 can be larger. Providing the first strut 1926 with two bearings, the first slot bearing 1925 and the first hole bearing 1927, reduces the overall size of each bearing by 50% over that needed to support the same load with a single bearing joint. The first strut 1926 can be of smaller size in terms of bearing diameter, bearing width, or a combination thereof. The smaller version of the first strut 1926 can be used in the snake wrist structure 110 with a thinner first rim 1971 resulting in an increased diameter of the snake wrist lumen 1390. If the snake wrist lumen 1993 is larger, the amount of cables and payload in the snake wrist lumen 1993 can be increased to provide additional capability for the snake wrist structure 110.

The first toothed gear 1912 can include a first toothed gear coating 2139 on the surface of the first toothed gear 1912 to reduce friction between the first joint disk 1902 and the second joint disk 1932. The first toothed gear coating 2139 is defined as a wear resistant material over the surface of the first toothed gear 1912. For example, the first toothed gear 1912 can be manufactured of a variety of medical grade metal alloys. The medical grade metal alloys composition can include Nitronic 60, surgical stainless steel, titanium, nickel, chromium, molybdenum, or a combination thereof. The first toothed gear 1912 can include a wear-resistant coating on the tooth to prevent galling and wear. The first toothed gear coating 2139 can be a variety of medical grade wear-resistant coatings such as diamond-like carbon, thin dense chromium, fluropolymer, or Medcoat 2000.

It has been discovered that the present invention provides the medical instrument 100 with improved durability and wear resistance. Including a first toothed gear coating 2139 on the surface of the first toothed gear 1912 can prevent galling and wear on the first strut 1926, leading to an extended operational life of the snake wrist structure 110. The wear-resistant coating can reduce friction between the first joint disk 1902 and the second joint disk 1932 resulting in less wear that can allow the use of softer materials in the manufacture of the first strut 1926.

Figure 22:
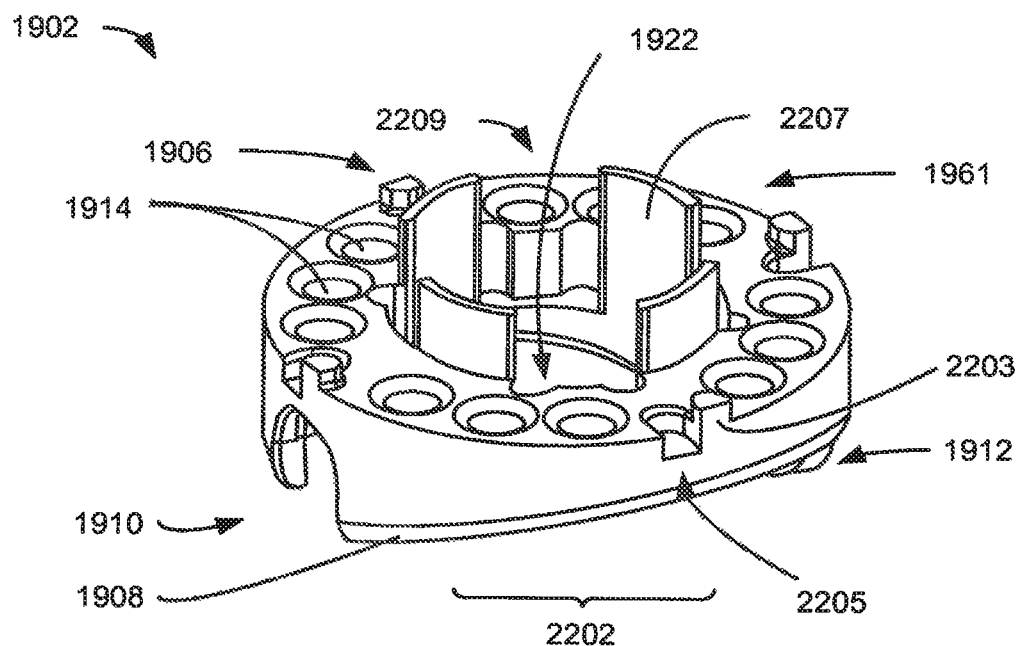
FIG. 22 is an isometric view of the bottom of the first joint disk in a fourth embodiment.

Referring now to FIG. 22 therein is shown an isometric view of the bottom of the first joint disk 1902 in a fourth embodiment. The first joint disk 1902 can include the first cable holes 1914, the first alignment keys 1906, and the first inner interlock structure 1961.

The first joint disk 1902 can include an interlocking structure on the bottom of the first joint disk 1902 for connecting the first joint disk 1902 to another disk element or other mounting structure. The interlocking structure can hold the first joint disk 1902 and another disk element in a fixed orientation. The interlocking structure can include a variety of mating structures including the first alignment keys 1906 with an first alignment key tab 2203 and the first alignment key hole 2205, a rib and slot structure, a pin and hole structure, a grooved structure, or a combination thereof.

For example, the first alignment keys 1906 are four interlocking structures positioned at 90 degree intervals around the bottom of the first joint disk 1902. One of the first alignment keys 1906 is under the first tooth slot 1910. One of the first alignment keys 1906 is opposite the first tooth slot 1910 and under the first toothed gear 1912. The other two first alignment keys 1906 are under the lowest points of the first angled surface 1908.

The first joint disk 1902 can include the first cable holes 1914 arranged around the first inner opening 1922. The first cable holes 1914 are arranged between the first alignment keys 1906 and evenly distributed between each adjacent pair of the first alignment keys 1906. The first cable holes 1914 can have a beveled edge on the bottom of the first joint disk 1902.

The first joint disk 1902 can include the first inner interlock structure 1961. The first inner interlock structure 1961 can include the first inner interlock ribs 2207 and first inner interlock slots 2209.

The first joint disk 1902 can include the first inner opening 1922. The first inner opening 1922 is an opening in a central portion 2202 of the first joint disk 1902. The central portion 2202 is defined as the interior part of the first joint disk 1902 surrounding the central axis 119 of FIG. 1.

Figure 23:
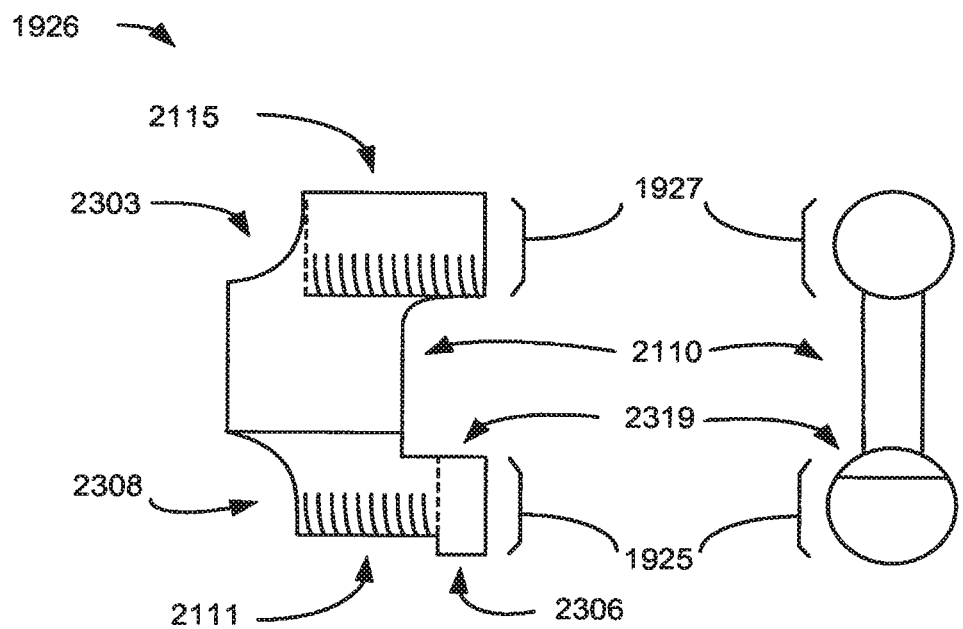
FIG. 23 is a side and front view of the first strut.

Referring now to FIG. 23 therein is shown a side and front view of the first strut 1926. The first strut 1926 can include the first slot bearing 1925, the first connection link 2110, and the first hole bearing 1927.

The first slot bearing 1925 is roughly cylindrical. The first strut 1926 can include a first landing surface 2319 facing the first hole bearing 1927. The first landing surface 2319 can include a flat surface facing the first hole bearing 1927. The first slot bearing 1925 can include a first locking lip 2306 on the outer edge of the first slot bearing 1925 on the side facing away from the first hole bearing 1927.

The first strut 1926 can include a first slot locking notch 2308 on the inner edge of the first slot bearing 1925. The first slot bearing 1925 can include a first slot bearing surface 2111 on the side of the first slot bearing 1925 facing away from the first hole bearing 1927.

The first strut 1926 can include the first connection link 2110 between the first slot bearing 1925 and the first hole bearing 1927. The first connection link 2110 is directly connected to the first slot bearing 1925 and the first hole bearing 1927.

The first hole bearing 1927 is roughly cylindrical. The first strut 1926 can include a first hole locking notch 2303 on the inner edge of the first hole bearing 1927. The first hole bearing 1927 can include a first hole bearing surface 2115 on the side of the first hole bearing 1927 facing away from the first slot bearing 1925.

The snake wrist structure 110 of FIG. 1 can be in a variety of configurations. For example, the snake wrist structure 110 can be placed under stress during operation. In one scenario, 12 joint control cables can exert a force of 160 Newtons per joint control cable for a total force of 1920 Newtons. Estimating a one half load on each strut, gives 960 Newtons per strut. Given per first strut 1926 where the bearing surfaces of the bearings are $A_{b1}=2.1947$ mm$^2$ and $A_{b2}=1.716123$ mm$^2$ For example, the snake wrist structure 110 can include a configuration where the snake wrist structure consisting of repeating identical single-degree of freedom joints connected in series with joint axes orthogonal to the central axis of the instrument shaft and either parallel or orthogonal to adjacent identical single-degree of freedom joints as dictated by the desired degrees of freedom and range of motion of the snake wrist structure. The repeating single-degree of freedom joint structure includes: a first joint disk having a first rim having a first tooth slot and a first toothed gear with the first tooth slot opposite the first toothed gear along the first rim; and a first strut having a first slot bearing and a first hole bearing connected by a first connection link with the first slot bearing in the first tooth slot, whereby an articulated joint is formed by connecting two pairs of first joint disk and first struts together with a 180 degree relative orientation to one another and locking said combination of first joint disks and first struts together by mating additional repeating single degree of freedom joints in series.

Figure 24:
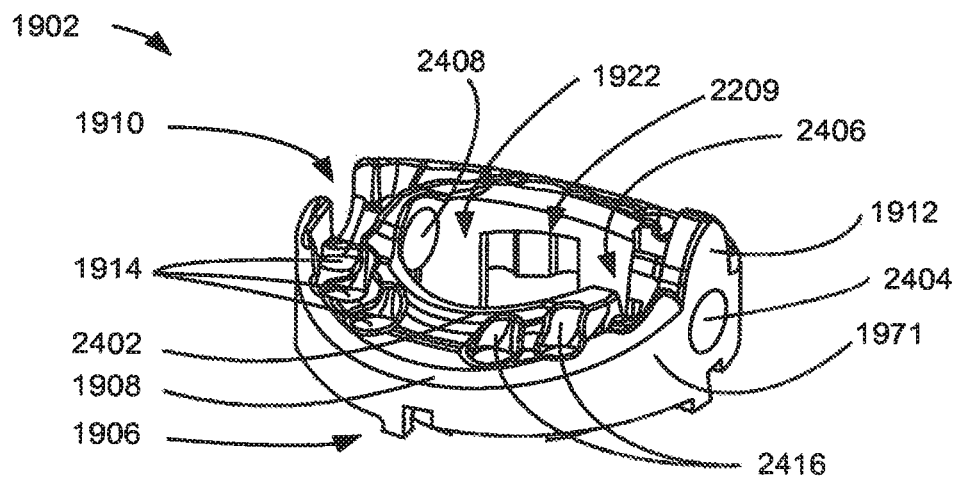
FIG. 24 is an isometric view of the first joint disk in a fourth embodiment.

Referring now to FIG. 24 therein is shown an isometric view of the first joint disk 1902 in a fourth embodiment. The first joint disk 1902 can include the first alignment keys 1906, the first angled surface 1908, the first toothed gear 1912, the first tooth slot 1910, the first rim 1971, the first inner opening 1922, the first cable holes 1914, the first cable cutouts 2416, and the first inner interlock slots 2209.

The first joint disk 1902 can include a first inner ring 2402, the first bearing hole 2404, the first bearing slot 2406, a first bearing mounting hole 2408. The first inner ring 2402 is defined as a raised structural element of the first joint disk 1902 around and forming the first inner opening 1922. The first inner ring 2402 can be a raised ridge between the first cable holes 1914 and the first inner opening 1922.

The first bearing slot 2406 is defined as a structural element for supporting the inner side of the first slot bearing 1925 of FIG. 19. The first bearing slot 2406 can be a concave opening in the first inner ring 2402. The first bearing slot 2406 is adjacent to the first toothed gear 1912.

The first bearing mounting hole 2408 is defined as a structural element for supporting the inner side of the second hole bearing 2127 of FIG. 21. The first bearing mounting hole 2408 can be an hole in the first inner ring 2402. The first bearing mounting hole 2408 is adjacent to the first tooth slot 1910.

The first joint disk 1902 can include the first toothed gear 1912 on the first rim 1971. The first bearing hole 2404 is directly below the first toothed gear 1912 between the first toothed gear 1912 and one of the first alignment keys 1906 on the bottom side of the first joint disk 1902. A first bearing slot 2406 is on the first inner ring 2402 on the same side as the first toothed gear 1912.

The first joint disk 1902 can include the first tooth slot 1910 on the first rim 1971 opposite from the first toothed gear 1912. The first joint disk 1902 can include the first bearing mounting hole 2408 on the first inner ring 2402 on the same side as the first tooth slot 1910.

The first joint disk 1902 can include the first cable holes 1914 and the first cable cutouts 2416 between the first rim 1971 and the first inner ring 2402. The first inner ring 2402 is around the first inner opening 1922. The first inner opening 1922 is between the first bearing slot 2406 and the first bearing mounting hole 2408.

It has been discovered that the present invention thus has numerous aspects.

A principle aspect that has been unexpectedly discovered is that the present invention can provide a simplified mechanism for forming a snake wrist structure for medical instruments. Embodiments of the present invention have been found to reduce the number of parts required for the snake wrist structure to a joint disk, a locking element, and a strut.

Another aspect is the present invention utilizes only standard assembly processes, yet is extremely reliable. The finished snake wrist structure can be made with a smaller diameter and no additional space is required to implement the present invention.

The resulting method, process, apparatus, device, product, and/or system is straightforward, cost-effective, uncomplicated, highly versatile, accurate, sensitive, and effective, and can be implemented by adapting known materials and processes for ready, efficient, and economical manufacturing, application, and utilization.

Another important aspect of the present invention is that it valuably supports and services the historical trend of reducing costs, simplifying systems, and increasing performance.

These and other valuable aspects of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A medical instrument comprising:
 a joint disk comprising a rim;
 the rim comprising a tooth gear extending from a second portion of the rim;
 the rim comprising a tooth slot extending into the rim from a first portion of the rim, the first portion of the rim opposite the second portion of the rim, the tooth slot being configured to receive a slot bearing of a first strut; and
 the rim comprising a bearing hole configured to receive a hole bearing of a second strut, the second strut being different from the first strut.

2. The medical instrument of claim 1, wherein:
 the rim comprises an alignment rib extending from the rim; and
 the rim comprises an alignment slot extending into the rim.

3. The medical instrument of claim 2, wherein:
 the joint disk is a first joint disk, the rim is a first rim, the tooth gear is a first tooth gear, the tooth slot is a first tooth slot, the alignment rib is a first alignment rib, and the alignment slot is a first alignment slot;
 the medical instrument further comprises a second joint disk comprising a second rim;
 the second rim comprises a second tooth gear extending from a first portion of the second rim;
 the second rim comprises a second tooth slot extending into the second rim from a second portion of the second rim;
 the second rim comprises a second alignment rib extending from the second rim;
 the second rim comprises a second alignment slot extending into the second rim;
 the first alignment rib of the first rim is inserted into the second alignment slot of the second rim; and
 the second alignment rib of the second rim is inserted into the first alignment slot of the first rim.

4. The medical instrument of claim 3, wherein:
 the medical instrument further comprises a locking member, and the locking member comprises a tubular side wall;

the first joint disk defines a first inner opening;
the second joint disk defines a second inner opening; and
the tubular side wall is inserted into the first inner opening of the first joint disk and into the second inner opening of the second joint disk and secures the first joint disk to the second joint disk.

5. The medical instrument of claim 1, wherein:
the joint disk defines an inner opening.

6. The medical instrument of claim 5, wherein:
the inner opening extends through the joint disk along a central axis of the joint disk.

7. The medical instrument of claim 5, wherein:
the rim comprises one or more cable holes; and
the one or more cable holes are located radially outward from the inner opening relative to a central axis of the joint disk.

8. The medical instrument of claim 7, wherein:
the one or more cable holes are parallel with the central axis of the joint disk.

9. The medical instrument of claim 1, wherein:
the tooth gear comprises a convex shape; and
the tooth slot comprises a concave shape complimentary to the convex shape of the tooth gear.

10. The medical instrument of claim 1, wherein:
the rim comprises an angled surface; and
the angled surface extends at approximately 22.5 degrees relative to a plane orthogonal to a central axis of the joint disk.

11. The medical instrument of claim 1, wherein:
the medical instrument comprises the first strut and the second strut;
the first strut comprises the slot bearing, and the slot bearing is rotatably supported against the tooth slot; and
the second strut comprises the hole bearing, and the hole bearing is rotatably supported in the bearing hole.

12. The medical instrument of claim 11, wherein:
the hole bearing comprises a hole locking notch; and
the slot bearing comprises a slot locking notch.

13. The medical instrument of claim 1, wherein:
the tooth gear comprises a base in the second portion of the rim; and
the bearing hole is located at the base of the tooth gear.

14. The medical instrument of claim 13, wherein:
the slot bearing is a first slot bearing, the hole bearing is a first hole bearing,
the medical instrument further comprises the first strut and the second strut;
the first strut comprising the first slot bearing, the first hole bearing, and a first connection link, the first slot bearing being connected to the first hole bearing via the first connection link;
the second strut comprising a second slot bearing, a second hole bearing, and a second connection link, the second slot bearing being connected to the second hole bearing via the second connection link;
the first slot bearing of the first strut being rotatably supported against the tooth slot of the rim; and
the second hole bearing of the second strut being rotatably supported within the bearing hole of the rim.

15. The medical instrument of claim 14, further comprising:
a locking member;
the joint disk an inner opening;
the locking member comprising a tubular side wall, the tubular side wall being inserted into the inner opening of the joint disk; and
the locking member pressing against the second hole bearing while the second hole bearing is rotatably supported within the bearing hole of the rim.

16. A medical instrument comprising:
a plurality of joint disks;
each individual joint disk of the plurality of joint disks comprising means for pivotally coupling the individual joint disk to a second joint disk of the plurality of joint disks adjacent a first end portion of the individual joint disk; and
each individual joint disk of the plurality of joint disks comprising means for locking the individual joint disk to a third joint disk of the plurality of joint disks adjacent a second end portion of the individual joint disk reverse from the first end portion of the individual joint disk.

17. A medical instrument comprising:
a plurality of disks;
each individual one of the plurality of disks comprising means for pivotally coupling the individual one of the plurality of disks to another one of the plurality of disks;
each individual one of the plurality of disks comprising means for fixedly coupling the individual one of the plurality of disks to another one of the plurality of disks; and
each individual one of the plurality of disks defining an inner opening;
wherein on the condition that all disks of the plurality of disks are coupled via the means for pivotally coupling or the means for fixedly coupling, the inner openings of the plurality of disks together define a lumen that extends through the plurality of disks.

18. The medical instrument of claim 17, wherein:
the means for pivotally coupling comprises means located laterally outward from the lumen.

19. The medical instrument of claim 17, further comprising:
means for locking disks of the plurality of disks in a coupled state when coupled via the means for pivotally coupling.

20. The medical instrument of claim 17, wherein:
the means for pivotally coupling comprises means located laterally outward from the lumen;
the medical instrument further comprises means for locking disks of the plurality of disks in a coupled state when coupled via the means for pivotally coupling; and
the means for locking extends through the lumen adjacent the means for pivotally coupling.

21. The medical instrument of claim 17, wherein:
the means for pivotally coupling of a first disk of the plurality of disks defines a first pivot axis;
the means for pivotally coupling of a second disk of the plurality of disks defines a second pivot axis; and
on the condition that the first disk is coupled to the second disk via the means for fixedly coupling, the first pivot axis is orthogonal to the second pivot axis.

* * * * *